US011160505B2

(12) United States Patent
Gunasekar et al.

(10) Patent No.: US 11,160,505 B2
(45) Date of Patent: Nov. 2, 2021

(54) SYSTEM AND METHOD FOR TESTING CONTACT QUALITY OF ELECTRICAL-BIOSIGNAL ELECTRODES

(71) Applicant: Zeto, Inc., Santa Clara, CA (US)

(72) Inventors: Aswin Gunasekar, San Jose, CA (US); Ferenc Benedek, Szeged (HU); János Kokavecz, Kiskoros (HU); Gabor Braun, Salgótarján (HU)

(73) Assignee: Zeto, Inc., Santa Clara, CA (US)

( * ) Notice: Subject to any disclaimer, the term of this patent is extended or adjusted under 35 U.S.C. 154(b) by 0 days.

(21) Appl. No.: 16/854,568

(22) Filed: Apr. 21, 2020

(65) Prior Publication Data
US 2020/0245942 A1 Aug. 6, 2020

Related U.S. Application Data

(63) Continuation of application No. 15/799,792, filed on Oct. 31, 2017, now Pat. No. 10,660,572, which is a
(Continued)

(51) Int. Cl.
*A61B 5/291* (2021.01)
*A61B 5/00* (2006.01)

(52) U.S. Cl.
CPC ............ *A61B 5/6843* (2013.01); *A61B 5/291* (2021.01); *A61B 5/7246* (2013.01); *A61B 5/6803* (2013.01); *A61B 5/684* (2013.01); *A61B 5/742* (2013.01); *A61B 5/743* (2013.01); *A61B 2562/0209* (2013.01)

(58) Field of Classification Search
CPC ... A61B 5/6843; A61B 5/0478; A61B 5/7246; A61B 5/743; A61B 5/684; A61B 5/742; A61B 2562/0209; A61B 5/6803; A61B 5/0476; A61B 5/291; A61B 5/25;
(Continued)

(56) References Cited

U.S. PATENT DOCUMENTS 5,042,498 A * 8/1991 Dukes .................. A61B 5/0424
600/509
6,636,754 B1 * 10/2003 Baura ................ A61B 5/02028
600/393
(Continued)

FOREIGN PATENT DOCUMENTS

WO WO-2008056309 A2 * 5/2008 ........... A61B 5/0424

*Primary Examiner* — Jacqueline Cheng
*Assistant Examiner* — Tho Q Tran
(74) *Attorney, Agent, or Firm* — Run8 Patent Group; Peter Miller

(57) ABSTRACT

One variation of a method for testing contact quality of electrical-biosignal electrodes includes: outputting a drive signal through a driven electrode, the drive signal comprising an alternating-current component oscillating at a reference frequency and a direct-current component; reading a set of sense signals from a set of sense electrodes at a first time; calculating a first combination of the set of sense signals; calculating a first direct-current value comprising a combination of the first combination and the direct-current component of the drive signal at approximately the first time; and at a second time succeeding the first time, shifting the direct-current component of the drive signal output by the driven electrode to the first direct-current value.

19 Claims, 10 Drawing Sheets

Related U.S. Application Data continuation-in-part of application No. 15/351,016, filed on Nov. 14, 2016, now Pat. No. 10,799,180.

(60) Provisional application No. 62/255,401, filed on Nov. 14, 2015.

(58) Field of Classification Search
CPC ......... A61B 5/369; A61B 5/6868; A61B 5/31; A61B 5/384; A61B 5/251
USPC .......................................................... 600/544
See application file for complete search history.

(56) References Cited

U.S. PATENT DOCUMENTS

| | | | |
|---|---|---|---|
| 2002/0188216 A1* | 12/2002 | Kayyali ............... | A61B 5/0478 600/544 |
| 2003/0083584 A1* | 5/2003 | Yonce .................. | A61B 5/6843 600/509 |
| 2009/0259137 A1* | 10/2009 | Delic .................. | A61B 5/0478 600/545 |
| 2011/0112418 A1* | 5/2011 | Feild .................... | A61B 5/0432 600/509 |
| 2014/0088394 A1* | 3/2014 | Sunderland .......... | A61B 5/0492 600/373 |
| 2019/0274568 A1* | 9/2019 | Shahdoostfard ..... | A61B 5/7221 |

* cited by examiner

SYSTEM AND METHOD FOR TESTING CONTACT QUALITY OF ELECTRICAL-BIOSIGNAL ELECTRODES

CROSS-REFERENCE TO RELATED APPLICATIONS

This application is a continuation application of U.S. patent application Ser. No. 15/799,792, filed on 31 Oct. 2017, which is a continuation-in-part application of U.S. patent application Ser. No. 15/351,016, filed on 14 Nov. 2016, which claims the benefit of U.S. Provisional Application No. 62/255,401, filed on 14 Nov. 2015, both of which are incorporated in their entireties by this reference.

TECHNICAL FIELD

This invention relates generally to the field of electroencephalography and more specifically to a new and useful system and method for testing contact quality of electrical-biosignal electrodes in the field of electroencephalography.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. Methods

Figure 1:
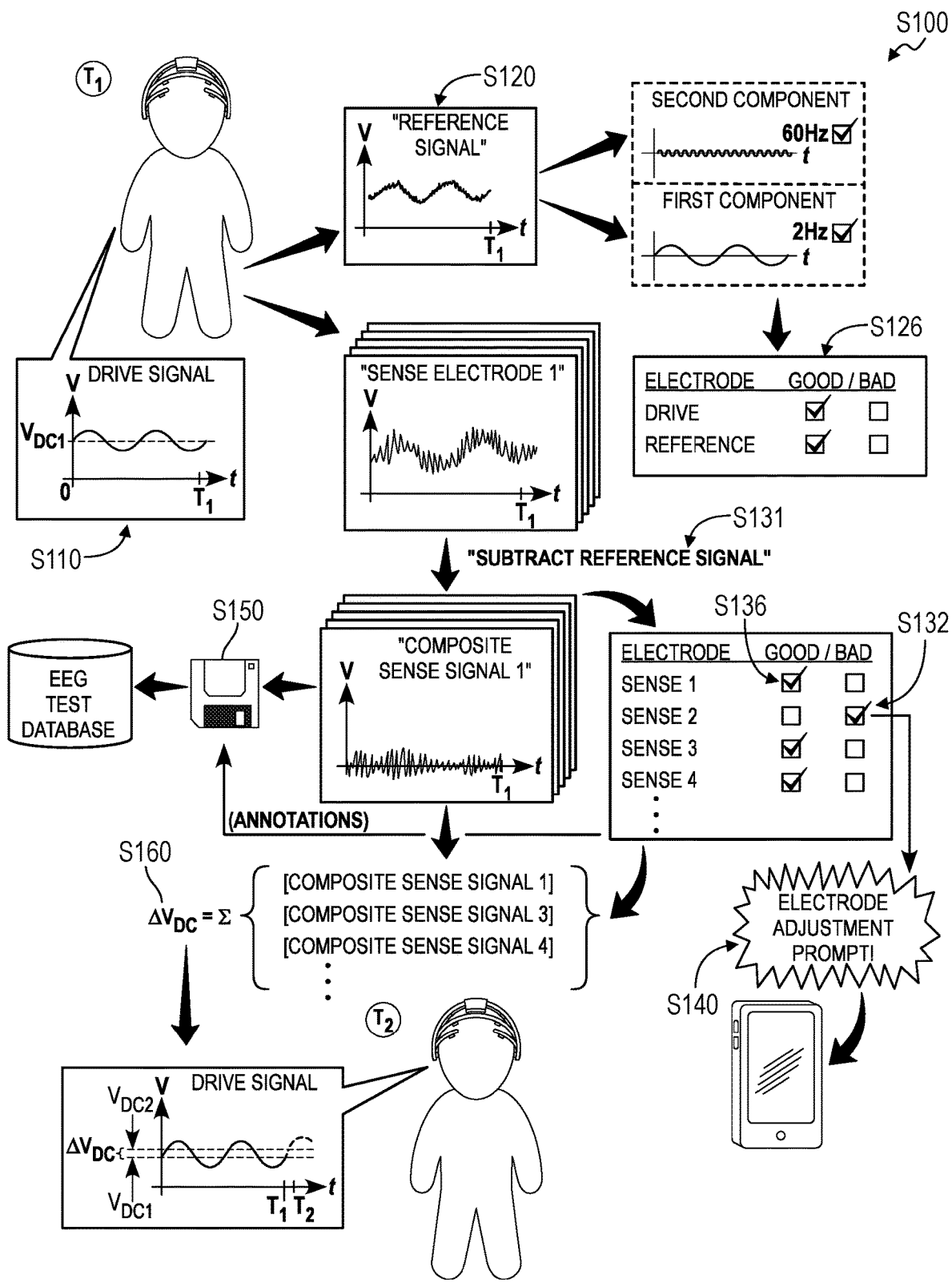
FIG. 1 is a flowchart representation of a method.
Figure 2A:
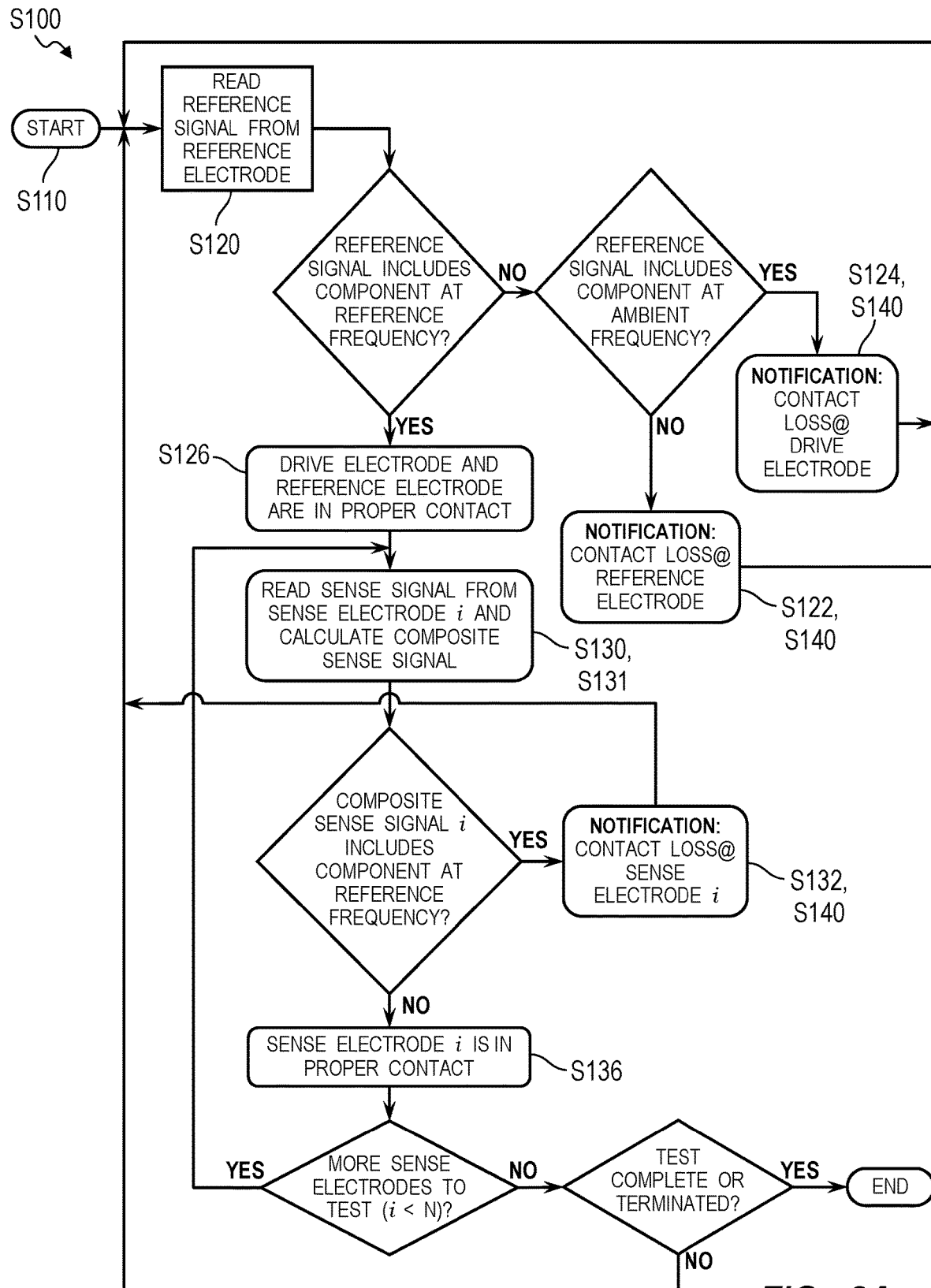
FIGS. 2A, 2B, and 2C are flowchart representations of variations of the method.
Figure 2B:
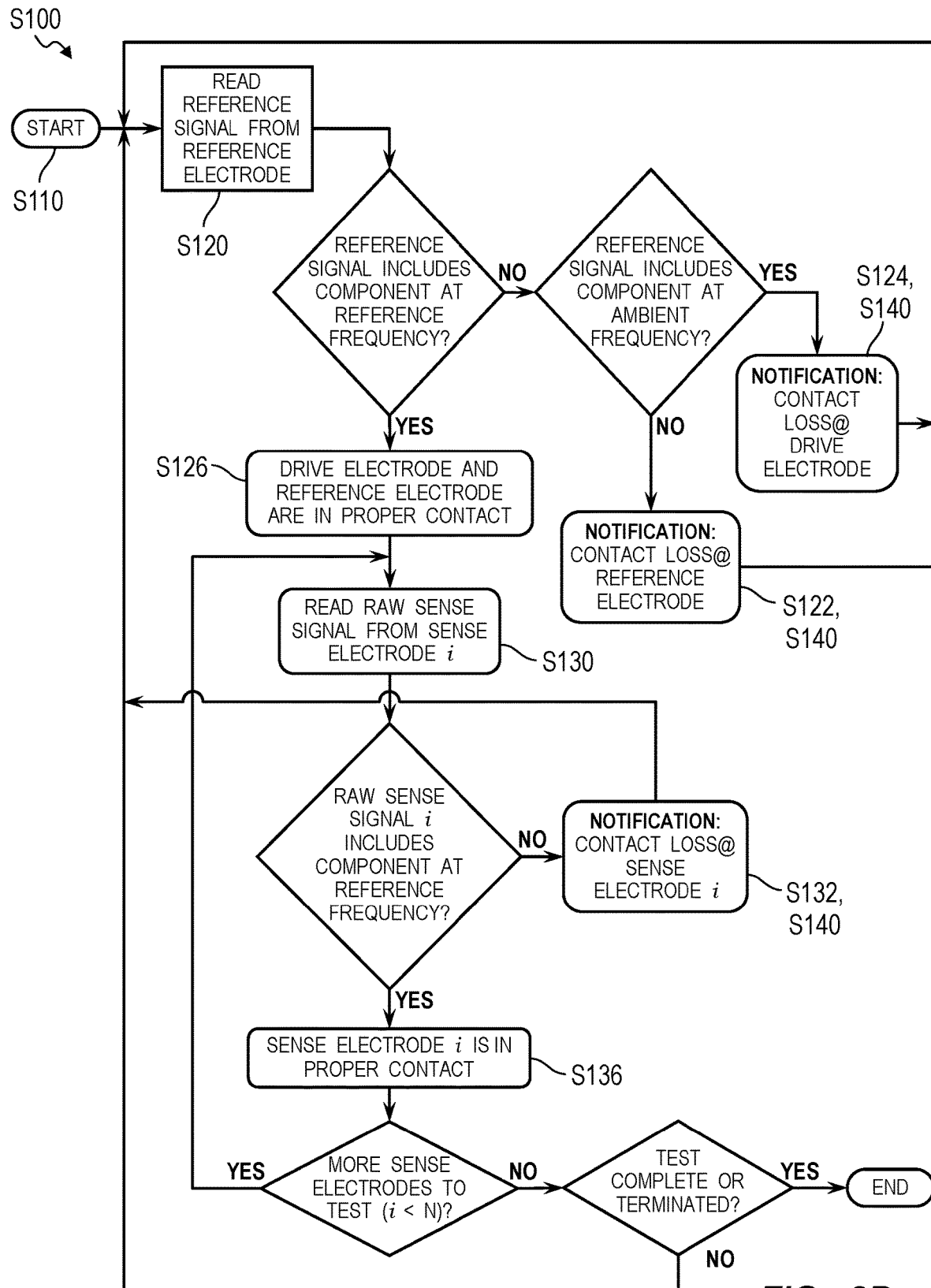

As shown in FIGS. 1 and 2B, a method for testing contact quality of electrical-biosignal electrodes includes: outputting a drive signal through a driven electrode 110 in Block S110, the drive signal including an alternating-current component oscillating at a reference frequency and a direct-current component; reading a reference signal from a reference electrode 120 in Block S120; in response to the raw reference signal excluding a first signal component oscillating at the reference frequency and excluding a second signal component oscillating at an ambient frequency, determining that the reference electrode 120 is in improper contact with a user's skin in Block S122; in response to the raw reference signal excluding the first signal component oscillating at the reference frequency and including the second signal component oscillating at the ambient frequency, determining that the driven electrode 110 is in improper contact with the user's skin in Block S124; reading a first sense signal from a first sense electrode 131 in Block S130; in response to the raw reference signal including the first signal component oscillating at the reference frequency and in response to the first sense signal excluding a third signal component oscillating at the reference frequency, determining that the first sense electrode is in improper contact with the user's skin in Block S132; and in response to determination of improper contact between the user's skin and one of the driven electrode 110, the reference electrode 120, and the first sense electrode, generating an electrode adjustment prompt in Block S140.

Figure 2C:
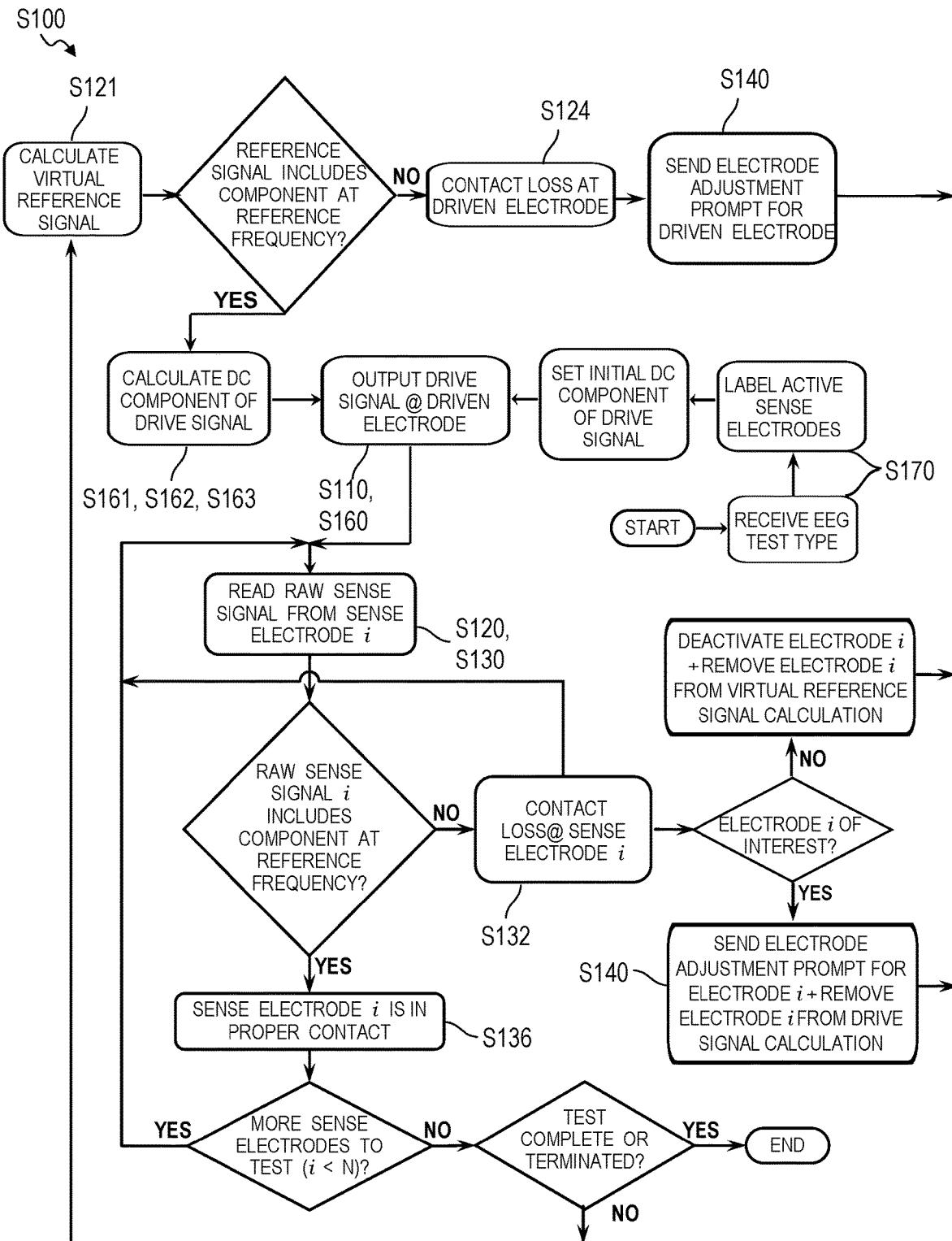

One variation of the method shown in FIG. 2C includes: outputting a drive signal through a driven electrode in Block Silo, the drive signal including an alternating-current component oscillating at a reference frequency and a direct-current component; reading a set of sense signals from a set of sense electrodes, the set of sense signals including a first sense signal detected by a first sense electrode in the set of sense electrodes in Block S130; calculating a combination of the set of sense signals in Block S121; in response to the combination excluding a first signal component oscillating at the reference frequency and including a second signal component oscillating at an ambient frequency, determining that the driven electrode is in improper contact with a user's skin in Block S124; in response to the combination including the first signal component oscillating at the reference frequency and in response to the first sense signal excluding a third signal component oscillating at the reference frequency, determining that the first sense electrode is in improper contact with the user's skin in Block S132; and in response to determination of improper contact between the user's skin and one of the driven electrode and the first sense electrode, generating an electrode adjustment prompt in Block S140.

Another variation of the method shown in FIG. 2C includes: receiving selection of a set of channels of interest in Block S170; selecting a first subset of sense electrodes, in a set of sense electrodes integrated into an electroencephalography headset, corresponding to the set of channels of interest in Block S170; selecting a second subset of sense electrodes, in the set of sense electrodes, differing from the first subset of sense electrodes in Block S170; during a test period, outputting a drive signal through a driven electrode integrated into the electroencephalography headset in Block S110, the drive signal including an alternating-current component oscillating at a reference frequency and a direct-current component; and, over a first duration of a test period, reading a first set of sense signals from the first subset of sense electrodes in Block S130, reading a second set of sense signals from the second subset of sense electrodes in Block S120, adjusting the direct-current component of the drive signal to follow a first combination of the first subset of sense signals in Block S160, calculating a virtual reference signal as a function of the second set of sense signals in Block S121, and recording differences between the first set of sense signals and the virtual reference signal in Block S150.

2. Applications

Generally, the method S100 can be implemented by an electrical biosignal acquisition system 100 to systematically characterize the quality of contact between electrodes—in the electrical biosignal acquisition system 100—and a user's skin and to automatically provide guidance for improving such contact quality, such as to a technician overseeing the user or to the user directly. In particular, the electrical biosignal acquisition system 100 executing the method S100 can output a drive signal containing an AC component through the driven electrode 110 in contact with the user's skin and then determine the quality of contact between the user's skin and the driven electrode 110, the reference electrode 120, and a set of sense electrodes based on the presence of a like AC component in raw reference and sense signals collected by the reference and sense electrodes, respectively. The driven electrode 110 can output a drive signal containing an AC component oscillating at a frequency distinct from a frequency of common ambient electromagnetic noise (e.g., 60 Hz continuous AC noise in North America, 50 Hz continuous AC noise in Europe) and unique to oscillating electrical signals generated by a living (e.g., human) body such that alternating components in each of the raw reference and sense signals can be correlated with (e.g., matched to) the AC component of the drive signal—entering the body at the driven electrode 110—with a high degree of accuracy. For example, the electrical biosignal acquisition system 100 can output a drive signal containing a DC component of 2.5V and an AC component characterized by a sinusoidal, 2.0 Hz, 1.7-millivolt peak-to-peak AC signal; and the electrical biosignal acquisition system 100 can correlate the presence of a 2.0 Hz AC signal in each of the raw reference and sense signals with the quality of contact between the user's skin and the reference and sense electrodes, respectively.

In one example, Blocks of the method S100 can be executed by an electroencephalogram (EEG) headset including 19 sense electrodes, one driven (e.g., "driven right leg") electrode, and one reference electrode 120, as described below, to determine whether the sense, driven, and reference electrode are in proper contact with a patient's skin during administration of an EEG test. In this example, the EEG headset 102 can drive the driven electrode 110 at a reference frequency of 2.0 Hz and can determine: that the driven electrode 110 is in improper contact with the patient's (i.e., a user's) skin in Block S124 when the raw reference signal excludes a 2.0 Hz component but includes a 60 Hz component (a common ambient electromagnetic noise signal in North America); that the reference electrode 120 is in improper contact with the patient's skin in Block S122 when the raw reference signal excludes both a 2.0 Hz component and a 60 Hz component; and that a particular sense electrode 131 is in improper contact with the patient's skin in Block S132 when the driven and reference electrode are determined to be in proper contact with the patient's skin and when a sense signal output by the particular sense electrode 131 excludes a 2.0 Hz component (or when composite sense signal—including the raw reference signal subtracted from the raw sense signal—includes the 2.0 Hz component"). In this example, the EEG headset 102 can then broadcast a notification to an external connected device (e.g., a smartphone or tablet carried by a nurse, doctor, therapist, or epileptologist, etc. administering the EEG test) to notify an EEG test administrator of improper contact between a particular electrode and the patient's skin (hereinafter a "contact loss event"). In this example, the EEG headset 102 can additionally or alternatively flag or annotate data collected through each sense electrode 131 during an EEG test with the determined contact states of the driven electrode 110, reference electrode 120, and sense electrodes.

The EEG headset 102 can also implement Blocks of the method to calculate a "virtual" reference signal from one, a subset, or all active sense electrodes integrated into the EEG headset 102, thereby reducing a total number of electrodes in the EEG headset 102 and reducing complexity in manufacture and setup of the EEG headset 102 on a user's head. Furthermore, the EEG headset 102 can selectively activate a subset of sense electrodes during an EEG test, such as a first subset of sense electrodes that correspond to channels of interest specified in an EEG test configured by an EEG test administrator. During this EEG test, the EEG headset 102 can record sense signals read by this first subset of sense electrodes to a digital file to the exclusion of other sense electrodes in the EEG headset 102. The EEG headset 102 can also selectively activate a second subset of sense electrodes during the EEG test, transform sense signals read from this second subset of sense electrodes into a virtual reference signal, analyze the virtual reference signal to confirm that the driven electrode is in proper contact with the user's skin, and reject noise in the channels of interest by subtracting the virtual reference signal from sense signals read from the first subset of sense electrodes.

The EEG headset 102 can also regularly adjust the DC component of the drive signal output by the driven electrode to follow the average center voltage of the sense electrodes in order to center these sense signals within the dynamic range of these sense electrodes. Therefore, the EEG headset 102 can execute Blocks of the method to selectively activate and deactivate sense electrodes, to selectively record sense signals corresponding to channels of interest, to selectively calculate virtual reference signals from multiple sense signals (e.g., corresponding or not corresponding to channels of interest), and to dynamically adjust the DC component of the drive signal to follow sense signals read from these sense electrodes (corresponding to channels of interest), thereby rejecting noise in recorded signals while also limiting rejection of relevant signals, ensuring that that peak-to-peak voltages at each sense electrode remain within the dynamic range of the sense electrodes (i.e., preventing "clipping"), and maintaining high signal quality during an EEG test.

The method S100 is described herein as executed by an EEG headset 102. For example, an EEG headset 102 can execute Blocks of the method S100 to detect and actively handle contact loss events by notifying an EEG test administrator of changes in contact quality at all or select electrodes substantially in real-time. The EEG headset 102 can additionally or alternatively handle contact loss events passively by annotating data collected by the sense (and reference) electrodes with contact loss events. However, the method S100 can be similarly executed by an electrocardiogram (ECG) system, an electromyogram (EMG) system, a mechanomyogram (MMG) system, an electrooculography (EOG) system, a galvanic skin response (GSR) system, and/or a magnetoencephalogram (MEG), etc.

3. System

Figure 3:
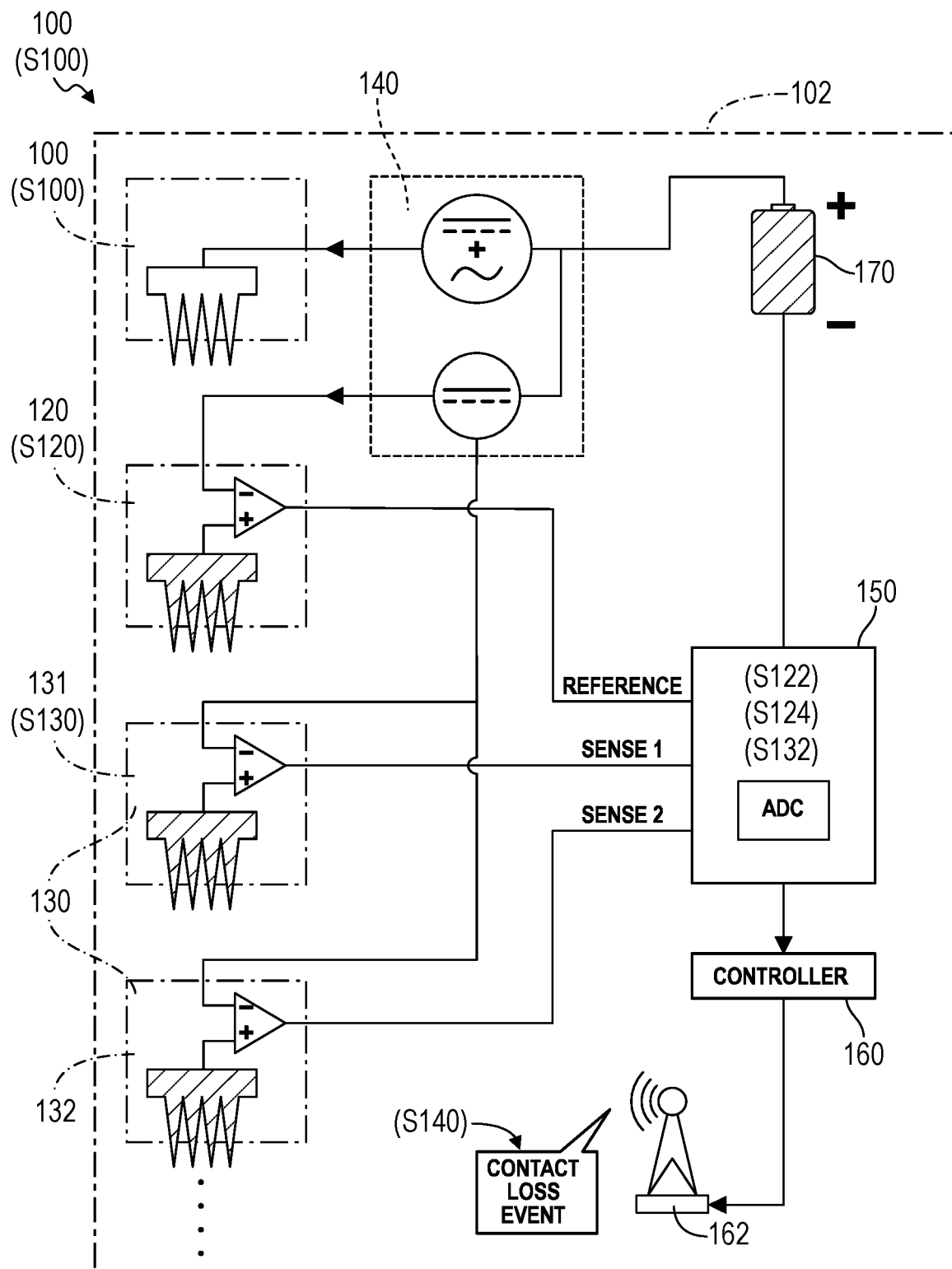
FIG. 3 is a schematic representation of a system.
Figure 4:
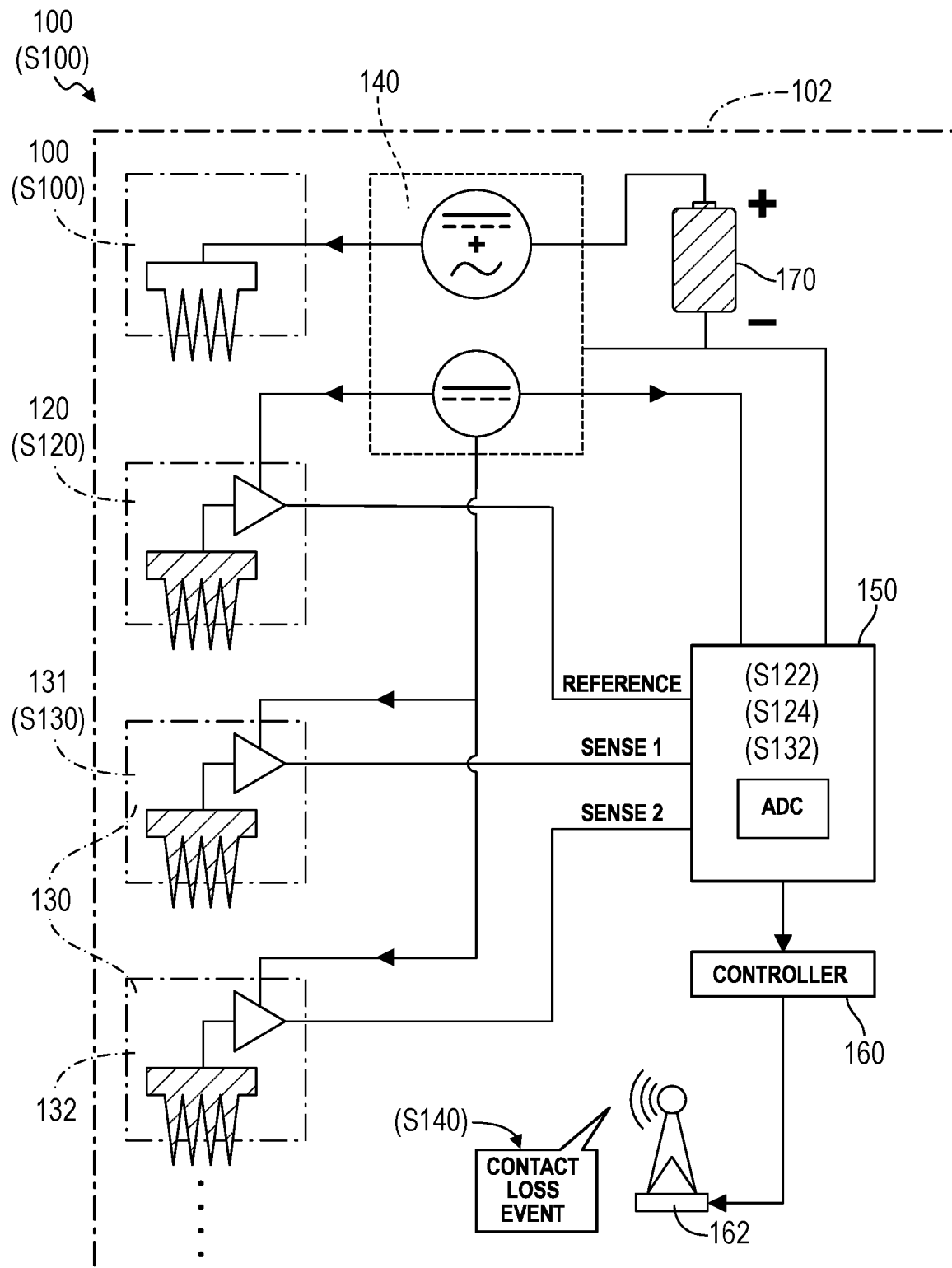
FIG. 4 is a schematic representation of one variation of the system.
Figure 5:
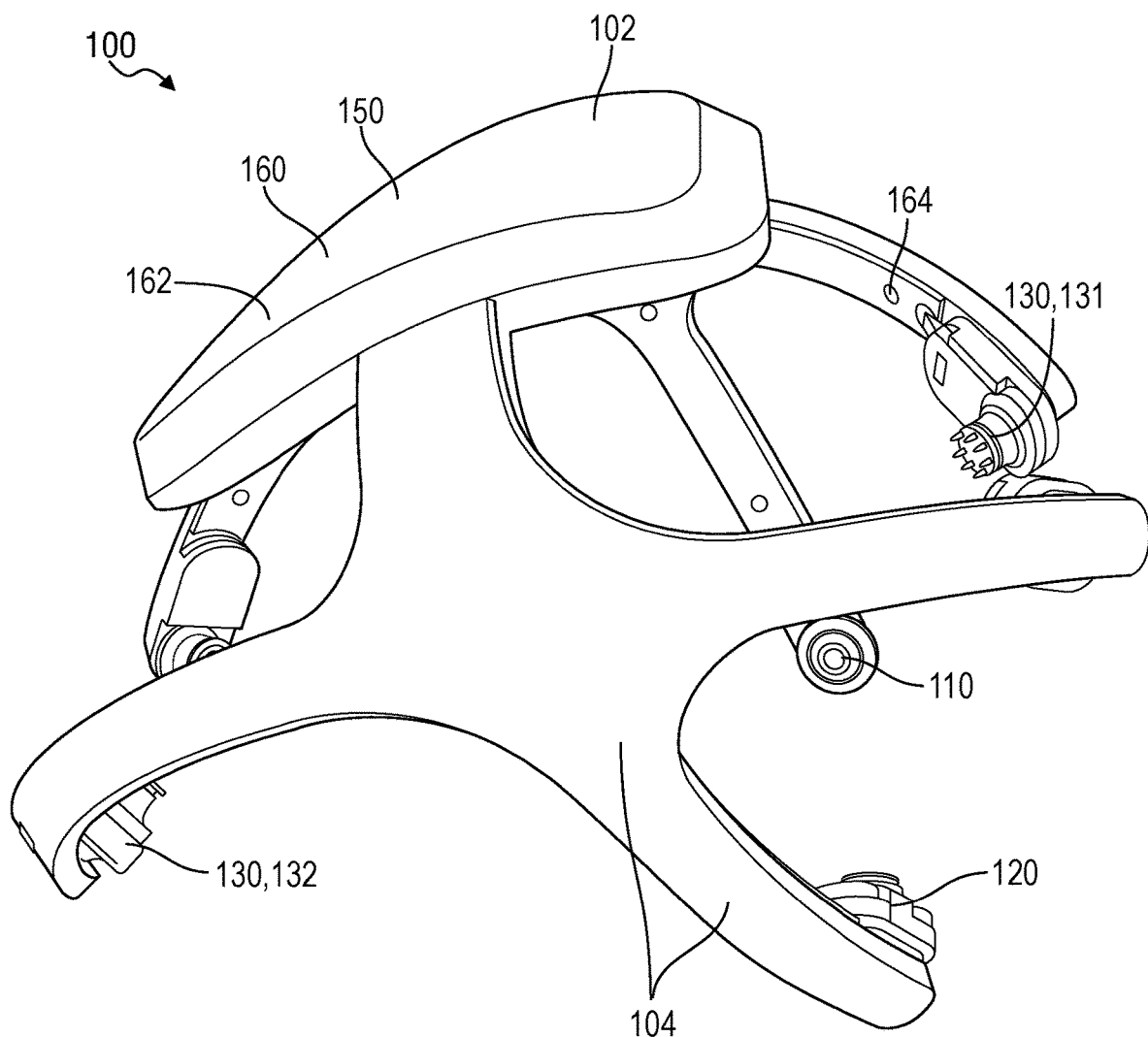
FIG. 5 is a schematic representation of one variation of the system.

As shown in FIGS. 3, 4, and 5, the method S100 can be executed by an electrical biosignal acquisition system 100, including: a driven electrode 110 electrically configured to contact skin of a user remotely from an area of interest; a signal generator 140 configured to output a drive signal oscillating at a reference frequency about a center voltage into the user via the driven electrode 110; a reference electrode 120 configured to contact skin of the user remotely from the area of interest and to detect a raw reference signal; a first sense electrode 131 configured to contact skin of the user at the area of interest and to detect a first raw sense signal from the area of interest; and a support structure 104 configured to support the driven electrode 110, the reference electrode 120, and the first sense electrode 131 on the user. The electrical biosignal acquisition system 100 also includes a signal processor 150 configured to: transform absence of a first signal component oscillating at the reference frequency in the raw reference signal and absence of a second signal component oscillating at an ambient frequency from the raw reference signal into confirmation that the reference electrode 120 is in improper contact with the user's skin; transform absence of the first signal component oscillating at the reference frequency and presence of the second signal component oscillating at the ambient frequency in the raw reference signal into confirmation that the driven electrode 110 is in improper contact with the user's skin; and to transform confirmation that the reference electrode 120 is in proper contact with the user's skin, confirmation that the driven electrode 110 is in proper contact with the user's skin, and absence of a third signal component oscillating at the reference frequency from the first raw sense signal into confirmation that the first sense electrode 131 is in improper contact with the user's skin. (Similarly, the signal processor 150 can transform confirmation that the reference electrode 120 is in proper contact with the user's skin, confirmation that the driven electrode 110 is in proper contact with the user's skin, and presence of a third signal component oscillating at the reference frequency in a first composite sense signal—representing a difference between the raw reference signal output by the reference electrode and the raw sense signal output by the first sense electrode—into confirmation that the first sense electrode 131 is in improper contact with the user's skin.)

The electrical biosignal acquisition system 100 is described herein as defining an EEG headset 102 configured to collect neural oscillation (or "brain wave") data from one or more sense electrodes when worn by a user. However, the electrical biosignal acquisition system 100 can include any other suitable type of biosensor electrode system. The electrical biosignal acquisition system 100 can also include one or more contact-based or non-contact sensors and can implement methods and techniques described herein to collect, process, and handle any such contact-based or non-contact sensor data.

4. Signal Generator and Driven Electrode

The signal generator 140 of the EEG headset 102 is configured to output a drive signal that includes a DC component and an AC component oscillating at a reference frequency; and the driven electrode 110 is electrically coupled to the signal generator 140, is configured to contact skin of a user, and outputs the drive signal into the user's skin. Generally, the signal generator 140 generates a drive signal that the driven electrode 110 then communicates into the body of the user to establish a known (or "reference") potential at the user's body relative to a power supply (e.g., a battery ground) within the EEG headset 102.

In one implementation, the EEG headset 102 includes a cage configured to support the driven electrode 110 against the user's skin but remotely from the user's head where electrical signals from brain activity (i.e., neural oscillations) predominate. For example, as shown in FIG. 5, the cage can include a beam extending downward from the top of the EEG headset 102, supporting the driven electrode 110, and configured to compress the driven electrode 110 against the right side of the user's neck when the EEG headset 102 is worn by the user. Alternatively, the driven electrode 110 can be mounted to the interior surface of a spring clip and connected to the cage via a flexible hookup wire, and the spring clip can be manually opened and released onto the user's right ear lobe after the EEG headset 102 is installed on the user's head.

The EEG headset 102 can also include a battery 170, and the signal generator 140 and the battery 170 can be arranged within a housing supported above or within the cage. The signal generator 140 can source current from the battery 170, convert this current into a drive signal oscillating at a reference frequency about a center voltage (e.g., a sinusoidal, 2.0 Hz, 1.7 millivolt peak-to-peak AC signal on a static or dynamic DC component of 2.5V), and then output this drive signal to the driven electrode 110 via a hookup wire, as shown in FIG. 3. The signal generator 140 and the driven electrode 110 can therefore cooperate to execute Block Silo of the method S100.

5. Reference Electrode

The reference electrode 120 is configured to contact skin of the user and to collect a reference signal from the user's body. Generally, the reference electrode 120 functions to conduct a reference signal from the user's skin into the signal processor 150, which then analyzes the raw reference signal to confirm connectivity (e.g., contact) between the user's skin and the driven electrode 110, the reference electrode 120, and one or more sense electrodes according to the method S100. The signal processor 150 within the EEG headset 102 can also implement common-mode rejection techniques to remove noise (e.g., artifacts) from sense signals collected by the sense electrodes by subtracting the raw reference signal from each raw sense signal in Block S131, as described below and shown in FIG. 2.

In one implementation, shown in FIGS. 3, 4, and 5, the reference electrode 120 includes a dry EEG electrode including: a substrate; a set of electrically-conductive prongs extending from a first side of the substrate; and an amplifier coupled to the substrate opposite the set of prongs and configured to amplify an electrical signal detected by the set of prongs. The electrically-conductive prongs can be elastic (e.g., gold-plated silicone bristles) or rigid (e.g., gold-plated copper prongs). The reference electrode 120 can alternatively include a flat or domed contact disk configured to contact the user's skin. Alternatively, the reference electrode 120 can be configured to accept interchangeable (e.g., magnetic) contact inserts, such as one of an elastic bristle insert, a rigid prong insert, a flat contact disk insert, and a domed contact disk insert.

In this implementation, the amplifier can include a differential op-amp including: a non-inverting input electrically coupled to the substrate; and an inverting input that receives the DC component of the drive signal from a DC output channel of the signal generator 140, as shown in FIG. 3. The amplifier can subtract the DC component of the drive signal from a high-impedance reference signal detected at the prongs, amplify the result (e.g., by a gain of 10, 1,000, or 10,000), and output the amplified result as a low-impedance reference signal that follows the high-impedance reference signal less the DC component of the drive signal and amplified by a gain value greater than 1. In this implementation, the output of the amplifier can be connected to the signal processor 150, which can receive the low-impedance reference signal from the reference electrode 120 and process this low-impedance reference signal to determine the contact state of the reference and driven electrode, as in Blocks S122 and S124, respectively.

Alternatively, the reference electrode 120 can include a non-inverting op-amp in a closed-feedback configuration characterized by a gain of ~1 and including a non-inverting input electrically coupled to the substrate in the reference electrode 120. In this example, the amplifier can include a buffer or a voltage follower (as shown in FIG. 4) and can receive a high-impedance reference signal from the set of prongs and output a low-impedance reference signal that follows the high-impedance reference signal directly. However, the reference electrode 120 can include any other type of dry- or wet-type EEG electrode.

Like the driven electrode 110 described above, the EEG headset 102 can support the reference electrode 120 against the user's skin and remotely from the user's head where electrical signals from brain activity are most present. In particular, because the signal processor 150 removes the raw reference signal from raw sense signals to form composite sense signals, the EEG headset 102 can support the reference electrode 120 against the user's skin substantially remotely from the sense electrodes and from the user's scalp, thereby minimizing collection of neural oscillations (e.g., "brain waves") by the raw reference signal, which would otherwise be rejected from the composite sense signals when the raw reference signal is subtracted from the raw sense signals in Block S131, as described below. For example and as shown in FIGS. 1 and 5, the case of the EEG headset 102 can include a second beam extending downward from the top of the EEG headset 102, supporting the reference electrode 120 opposite the driven electrode 110, and configured to compress the reference electrode 120 against the left side of the user's neck when the EEG headset 102 is worn by the user. Alternatively, like the driven electrode 110, the reference electrode 120 can be mounted to the interior surface of a second spring clip and connected to the cage via a second flexible hookup wire, and the second spring clip can be manually opened and released onto the user's ear left lobe after the EEG headset 102 is installed on the user's head.

Therefore, the driven electrode 110 can output a drive signal—including an AC component and a DC component—to establish a known, oscillating potential in the user's body during an EEG test in Block Silo. When in contact with the user's skin during the EEG test, the reference electrode 120 detects the drive signal, ambient noise, and/or other extraphysiologic artifacts and outputs these as a singular reference signal to the signal processor 150 in Block S120.

6. Sense Electrode

The EEG headset 102 also includes a sense electrode 131 configured to contact skin of the user and to pass neural oscillation data in the form of a sense signal from the user's skin into the signal processor 150. In the implementation described above in which the EEG headset 102 includes a cage, the cage can also support one or more sense electrodes 130 and can compress the sense electrodes 130 against the user's scalp when the EEG headset 102 is worn on the user's head. For example, the EEG headset 102 can include 19 sense electrodes 130 arranged in a 10-20 configuration, including two sense electrodes supported across a frontal polar site, four sense electrodes supported across a frontal lobe position, four sense electrodes supported across a temporal lobe position, five sense electrodes supported across lateral and longitudinal center axes, two sense electrodes supported across a parietal lobe position, and two sense electrodes supported across an occipital lobe position by the cage. However, the EEG headset 102 can include any other number of sense electrodes arranged in any other format or configuration.

Each sense electrode in the set of sense electrodes 130 can define a dry EEG electrode substantially similar to the reference electrode 120, such as including: a substrate; a set of electrically-conductive prongs extending from a first side of the substrate; and an amplifier coupled to the substrate opposite the set of prongs and configured to amplify an electrical signal passing through the set of prongs. Like the reference electrode 120 described above, when the EEG headset 102 is worn by the user, a sense electrode 131 can: contact the user's scalp; detect a high-impedance sense signal from the user's skin; convert the high-impedance sense signal into a low-impedance sense signal less the DC component of the drive signal (e.g., at a differential op-amp); and pass the low-impedance sense signal to the signal processor 150. The set of sense electrodes 130 can therefore be substantially similar, and each sense electrode 131 can be substantially similar to the reference electrode 120 such that the group of reference and sense electrodes output signals exhibiting similar gains, latencies, extraphysiologic artifacts, and/or intraphysiologic artifacts, etc.

However, the EEG headset 102 can include any other number and type of dry or wet sense electrodes.

7. Signal Processor

The EEG headset 102 also includes a signal processor 150 configured to: subtract a component of a raw reference signal output by the reference electrode 120 from a raw sense signal output by the sense electrode 131 to calculate a composite sense signal for the sense electrode 131 in Block S131; and to determine quality of contact between the driven electrode 110, the reference electrode 120, and each sense electrode 131 in the set of sense electrodes 130 based on the presence of components oscillating at the ambient frequency in the raw reference signal and based on presence of components oscillating at the reference frequency in the raw reference signal and in the sense signals. Generally, the signal processor 150 functions: to receive a raw reference signal from the reference electrode 120 and a raw sense signal from each of one or more sense electrodes in Blocks S120 and S130, respectively; to determine connectivity between the user's skin and the driven and reference electrode based on stability (or presence) of one or more AC components in the raw reference signal in Blocks S124 and S122, respectively; and—once the drive and reference electrodes are determined to be in proper contact with the user's skin—to determine connectivity between the user's skin and a sense electrode 131 based on the presence of an AC component characterized by the reference frequency in a corresponding raw sense signal (or absence of the AC component a corresponding composite sense signal) in Block S132.

In one implementation, the signal processor 150 includes an (multi-channel) analog-to-digital converter (ADC) that transforms a raw, low-impedance analog reference signal received from the reference electrode 120 into a raw digital reference signal (i.e., a digital value representing a voltage on the output channel of the reference electrode 120 for each sampling period). The signal processor 150 then computes a frequency (e.g., Fourier) transform of the digital reference signal, such as for a sampling period including one, two, four, or other number of cycles of the reference frequency. For example, for a reference frequency of 2.0 Hz, the signal processor 150 can compute the Fourier transform of the digital reference signal over a one-second sampling period, which may include two cycles of the AC component of the drive signal if the driven and reference electrode are in proper contact with the user's skin. In particular, if the frequency transform of the digital reference signal includes an AC component at the reference frequency, the signal processor 150 can determine that the driven and reference electrode are properly coupled via the user's skin and are therefore in proper contact with the user's skin for the sampling period. However, if the frequency transform of the digital reference signal excludes an AC component at the reference frequency, the signal processor 150 can determine that the driven and reference electrode are not properly coupled through the user and therefore that either or both the driven electrode 110 and the reference electrode 120 are not in proper contact with the user's skin.

In the foregoing implementation, if the frequency transform of the digital reference signal excludes both a first AC component at the reference frequency and a second AC component characterized by a common ambient electromagnetic noise frequency (e.g., 60 Hz in North America), the signal processor 150 can determine that the reference electrode 120 is in improper contact with the user's skin in Block S122. For example, the user's body may function as an RF collector (e.g., an "antenna") that collects ambient electromagnetic noise and communicates this electromagnetic noise into the reference electrode 120 when the reference electrode 120 is in proper contact with the user's skin. Therefore, for the EEG headset 102 used indoors in a lighted room in North America, if an oscillating (e.g., sinusoidal) 60 Hz signal component is not detected in the digital reference signal, the signal processor 150 can determine that (at least) the raw reference signal is in improper contact with the user's skin in Block S122.

However, if the frequency transform of the digital reference signal excludes an AC component at the reference frequency but includes an AC component at a frequency of persistent ambient electromagnetic noise, the signal processor 150 can determine that the driven electrode 110 is in improper contact with the user's skin in Block S124. In particular, for the EEG headset 102 used indoors in a lighted room in North America, if the reference electrode 120 is in proper contact with the user's skin but the driven electrode 110 is not, the digital reference signal may include a sinusoidal 60 Hz signal component but may exclude an AC component like the AC component output by the drive signal. The signal processor 150 can therefore determine the contact state of the driven electrode 110 in Block S124 based on the presence of (or lack of) certain AC signals in the raw reference signal.

For each sampling period during an EEG test, the ADC can also transform a raw, low-impedance analog sense signal received from a sense electrode 131 into a raw digital sense signal (i.e., a digital value representing a voltage on the output channel of the sense electrode 131 for each sampling period). The signal processor 150 can then subtract a digital value (e.g., a 32-bit value) of the digital reference signal from a digital value (e.g., also a 32-bit value) of the digital sense signal for the same sampling period to calculate a composite digital sense signal representing a voltage at the input side of the sense electrode 131 (i.e., a neural voltage relative to the reference signal) for the sampling period in Block S131. The signal processor 150 can repeat this process for each sense electrode 131 to calculate one composite digital sense signal per sense electrode 131 per sampling period during the EEG test.

Alternatively, the signal processor 150 can subtract the raw, low-impedance analog reference signal from the raw, low-impedance analog sense signal to calculate a composite analog sense signal in Block S131 and then pass this composite analog sense signal through the ADC. For example, each sense electrode 131 can include a differential op-amp: including an inverting input electrically connected to the output of the reference electrode 120; a non-inverting input electrically connected to the output of the sense electrode 131; and an output feeding into one channel of the ADC. In this example, the ADC can thus transform an output of the differential op-amp connected to the sense electrode 131 (i.e., a "composite analog sense signal") directly into a composite digital sense signal. The signal processor 150 can repeat this process for each sense electrode 131 to calculate one composite digital sense signal per sense electrode 131 per sampling period during the EEG test.

Because the raw reference signal and a raw sense signal output by a particular sense electrode 131 may include common ambient noise and other extraphysiologic and/or intraphysiologic artifacts, the signal processor 150 can achieve common-mode rejection by subtracting the raw reference signal (in raw low-impedance analog form or in raw digital form) from the raw sense signal for the particular sense electrode 131 in Block S131, thereby improving the signal-to-noise ratio (SNR) for each sense channel. Furthermore, because the reference electrode 120 is configured to contact the user's skin remotely from the scalp or other region of the user's head in which neural oscillations are commonly present (or present in greater amplitude), the raw reference signal may exclude a neural oscillation component or include only a very minor neural oscillation component such that neural oscillations in the composite sense signal are not rejected when the raw reference signal is subtracted from the sense signal in Block S131.

For each sense electrode 131, the signal processor 150 can then compute a frequency transform of the composite digital sense signal (e.g., for a sequence of composite digital sense signals over a period of time). In this implementation, if the driven and reference electrode are determined to be in proper contact with the user's skin, as described above, and if the frequency transform of the composite digital sense signal corresponding to a particular sense electrode 131 excludes an AC component at the reference frequency, the signal processor 150 can determine that the particular sense electrode 131 is in proper contact with the user's skin for the sampling period. In particular, the driven and sense electrodes couple via the user's body when both are in proper contact with the user's skin; the raw, low-impedance sense signal output by the sense electrode 131 therefore includes an AC component at the reference frequency when the drive and sense electrodes are in proper contact. When the reference electrode 120 is also in proper contact with the user's skin, the low-impedance reference signal output by the reference electrode 120 similarly includes an AC component at the reference frequency; therefore, when the low-impedance reference signal is subtracted from the raw, low-impedance sense signal in Block S131 and the result converted to digital form, the resulting composite digital sense signal excludes an AC component at the reference frequency. In particular, in Block S136, the signal processor 150 can determine that a sense electrode is in proper contact with the user's skin when: proper skin contact at the driven electrode is confirmed in Block S126; proper skin contact at the reference electrode is confirmed in Block S126; and the frequency transform of the composite digital sense signal of the sense electrode—calculated by subtracting the low-impedance reference signal from the low-impedance sense signal and digitizing the result in Block S131—excludes an AC component at the reference frequency, as shown in FIG. 2A.

However, if the driven and reference electrode are determined to be in proper contact with the user's skin and the frequency transform of the composite digital sense signal includes an AC component characterized by the reference frequency (which will be phased 180° from the AC component of the drive signal), the signal processor 150 can determine that the sense electrode 131 is not in proper contact with the user's skin in Block S132, as shown in FIG. 2A. In particular, when the sense electrode 131 is not in proper contact with the user's skin, the raw, low-impedance sense signal output by the sense electrode 131 excludes an AC component at the reference frequency. When the reference electrode 120 is in proper contact with the user's skin, the low-impedance reference signal output by the reference electrode 120 does include an AC component at the reference frequency; when the raw, low-impedance reference signal is then subtracted from the raw, low-impedance sense signal in Block S131 and the result digitized, the resulting composite digital sense signal includes an AC component at the reference frequency but phased at 180° from the drive signal, which the signal processor 150 can then interpret as improper contact between the user's skin and the sense electrode 131 in Block S132, as shown in FIG. 2A.

Therefore: an amplifier integrated into the reference electrode 120 can output a low-impedance reference signal that follows a high-impedance reference signal detected by prongs (or other contact surface) on the reference electrode 120; and the signal processor 150 can subtract a DC component of the drive signal from the low-impedance reference signal and represent this difference in a composite digital reference signal (e.g., as one digital value per sampling period) in Block S131. The signal processor 150 can then decompose the composite digital reference signal into a first set of oscillating signal components, such as by implementing frequency analysis techniques substantially in real-time to process a set of digital values representing the composite digital reference signal over a contiguous sequence of sampling periods. The signal processor 150 can then determine that the reference electrode 120 is in improper contact with the user's skin in Block S122 if the first set of oscillating signal components excludes both a first signal component oscillating at the reference frequency (e.g., 2 Hz) and a second signal component oscillating at an ambient frequency (e.g., approximately 60 Hz in North America, 50 Hz in Europe). Similarly, the signal processor 150 can determine that the driven electrode 110 is in improper contact with the user's skin in Block S124 if the first set of oscillating signal components excludes the first signal component oscillating at the reference frequency but includes the second signal component oscillating at the ambient frequency. However, the signal processor 150 can determine that the driven electrode 110 and the reference electrode 120 are in proper contact with the user's skin in Block S126 if the first set of oscillating signal components—extracted from the digital reference signal—includes the first signal component oscillating at the reference frequency.

Furthermore: an amplifier integrated into a sense electrode 131 can output a raw, low-impedance sense signal that follows a raw, high-impedance sense signal detected by prongs (or a contact surface) on the sense electrode 131; and the signal processor 150 can subtract the raw, low-impedance reference signal from the raw, low-impedance sense signal in Block S131 and digitize this difference to create a composite digital sense signal. (The signal processor 150 can alternatively subtract one digital reference value of a raw digital reference signal from a digital sense value of a raw digital sense signal recorded during the same sampling period for each sampling period during operation of the EEG headset 102 to create a composite digital sense signal for this sense electrode in Block S131.) The signal processor 150 can then decompose the composite digital sense signal into a second set of oscillating signal components, such as by implementing frequency analysis techniques in real-time to process a set of digital values representing the composite digital sense signal over a contiguous sequence of sampling periods. Once the signal processor 150 determines that the drive and reference electrode are in proper contact with the user's skin, the signal processor 150 can then determine that the sense electrode 131 is in improper contact with the user's skin in Block S132 if the second set of oscillating signal components includes a third signal component oscillating at the reference frequency (i.e., a third signal component oscillating at the reference frequency and phased at 180° from the AC component of the drive signal due to subtraction of the raw reference signal—containing a signal component oscillating at the reference frequency and in-phase within the drive signal—from the raw sense signal). However, the signal processor 150 can also determine that the sense electrode 131 is in proper contact with the user's skin in Block S136 if the second set of oscillating signal components excludes the third signal component oscillating at the reference frequency.

The signal processor 150 can test the skin connectivity of the driven electrode 110, the reference electrode 120, and the set of sense electrodes 130 serially and continuously throughout operation (e.g., throughout an EEG test), as shown in FIGS. 2A and 2B. A controller 160 can then handle detected loss of skin contact for all or a subset of electrodes in the EEG headset 102, as described below.

8. Virtual Reference Signal

One variation of the method shown in FIG. 2C includes: reading a second set of sense signals from a second subset of sense electrodes in Block S120; and calculating a combination of the set of sense signals and storing this combination as a virtual reference signal in Block S121. Generally, in this variation, the EEG headset 102 (or the native EEG test application described above) can generate a virtual reference signal from one or more sense electrodes—rather than read a reference signal from a dedicated reference electrode—and then implement methods and techniques described above to detect contact loss at the driven electrode and to calculate composite sense signals based on this virtual reference signal.

In one implementation, the signal processor 150: reads a raw analog sense signal from each sense electrode in the EEG headset 102 during a sampling period within an EEG test; transforms each raw analog sense signal into a raw digital sense signal at the ADC; calculates a combination (e.g., an average) of all raw digital sense signals for the sampling period; and stores this combination as a virtual reference signal for the sampling period. The signal processor 150 can then subtract the virtual reference signal from each raw digital sense signal to calculate composite digital sense signals for the sampling period (or for the next sampling period) and writes these composite digital sense signals to memory in Block composite digital sense signals in Block S150. The signal processor 150 can also analyze the virtual reference to determine when the driven electrode is in proper contact with the user's skin in Block S124, as described above. The signal processor 150 can repeat this process for each subsequent sampling period during the EEG test. The signal processor 150 can also fuse a previous virtual reference signal with raw digital sense signals detected during a next sampling period in order to damp signal noise between these sampling periods.

In a similar implementation, the signal processor 150 can calculate a virtual reference signal from sense signals read from a subset of sense electrodes during an EEG test. For example, for an EEG test designating the frontal lobe as an area of interest, the EEG headset 102 can: define a first subset of sense electrodes that includes FP1, FP2, F7, F3, FZ, F4, and F8 electrodes arranged across a frontal lobe region of the EEG headset 102; and define a second subset of sense electrodes that includes T5, P3, PZ, P4, and T6 electrodes arranged across temporal and parietal lobe regions of the EEG headset 102. In this example, the EEG headset 102 can thus define distinct, non-overlapping subsets of sense electrodes, wherein the first subset of sense electrodes span an area of interest on the user's scalp and wherein the second subset of sense electrodes are remote from this area of interest and span a region of the human head commonly exhibiting relatively minimal muscle movement. During execution of this EEG test, the EEG headset 102 can: calculate a virtual reference signal from sense signals read from the second subset of sense electrodes in Block S121; combine the virtual reference signal with sense signals from the first subset of sense electrodes to reject noise from these channels of interest; and record these composite digital sense signals from the first subset of sense electrodes to a digital file in Block S150 for subsequent analysis. By defining the second subset of sense electrodes that is distinct from the first subset of sense electrodes, the EEG headset 102 can calculate a virtual reference signal that includes substantially identical noise components as sense signals from the first subset of sense electrodes but that excludes relevant signals read from the first subset of sense electrodes over the area of interest. The signal processor 150 can thus achieve high selectivity in rejecting common mode noise from sense signals from the first subset of sense electrodes by subtracting the virtual reference signal from these sense signals. Similarly, by defining the second subset of sense electrodes over regions of the skull that frequently exhibit minimal muscle movement, the EEG headset 102 can calculate a virtual reference signal that is relatively free of muscle- and/or movement-type noise and that therefore represents a relatively highly accurate reference potential on the user's scalp.

In another example, the signal processor 150 can: define a default second subset of sense electrodes including the FZ, CZ, and PZ electrode arranged along the top-centerline of the skull and spanning a region of the human head commonly exhibiting relatively minimal muscle movement; and calculate a virtual reference signal from sense signals read from these three sense electrodes. If the FZ electrode is determined to have lost contact with the user's skin in Block S132 during execution of the EEG test, the signal processor 150 can dynamically deactivate the FZ electrode and remove the FZ sense signal from calculation of the virtual reference signal. The signal processor 150 can also: regularly reactivate, sample, and test the FZ electrode for return of proper contact, such as once per two-second interval; and reactive the FZ electrode and return the FZ sense signal to calculation of the virtual reference signal once proper contact between the FZ sense electrode and the user's skin returns. However, in this example, if the CZ sense electrode is determined to have lost contact with the user's skin in addition to the FZ sense electrode, the signal processor 150 can selectively activate (if previously inactive) an adjacent sense electrode (e.g., the C3 and/or C4 sense electrode), confirm contact quality of the sense electrode in Block S132, and inject a corresponding sense signal into calculation of the virtual reference signal. The signal processor 150 can therefore: dynamically remove sense signals of sense electrodes that have lost contact with the user's skin from calculation of the virtual reference signal; dynamically activate and inject sense signals from sense electrodes into calculation of the virtual reference signal; and dynamically deactivate sense electrodes based on the contact quality of each of these sense electrodes determined in Block S132.

Therefore, the signal processor 150 can populate a second subset of sense electrodes—for calculation of a virtual reference signal from their corresponding sense signals—based on an area of interest or specific channels of interest specified in a predefined or custom EEG test selected by an EEG test administrator. In particular, the signal processor 150 can select a predefined second subset of sense electrode based on a type of EEG test or a first set of sense electrodes selected by the EEG test administrator. Alternatively, the signal processor 150 can automatically select a custom second subset of sense electrodes based on a standard or custom first subset of sense electrodes selected for the upcoming EEG test, such as based on preset rules for populating the second subset of sense electrodes.

The signal processor 150 can also implement Block S132 to identify sense electrodes in the second subset of sense electrodes that have lost contact with the user's skin. When the signal processor 150 determines that a sense electrode in this second subset of sense electrodes has lost contact with the user's skin, the signal processor 150 can remove a corresponding sense signal from calculation of the virtual reference signal in Block S121 substantially in real-time and until proper contact between this sense electrode and the user's skin is reestablished and confirmed.

However, the signal processor 150 can implement any other method or technique to calculate a virtual reference signal from a fixed or dynamic set of one or more sense electrodes in the EEG headset 102 in Block S121. Furthermore, in this variation, the EEG headset 102 can default to reading and manipulating a reference signal read from the dedicated reference electrode 120, as described above; however, when the signal processor 150 determines that the reference electrode 120 has lost contact with the user's skin, the signal processor can deactivate the reference electrode 120 (or discard the reference signal read from the reference electrode 120) and dynamically transition to calculating a virtual reference signal from one or more sense signals in Block S121.

9. Controller

One variation of the EEG headset 102 further includes a controller 160 that handles instances of improper or poor contact between the user's skin and any of the drive, reference, and sense electrodes during operation (or "contact loss events"). Generally, the controller 160 can execute Block S140 of the method S100, which recites: in response to detection of improper contact between the user's skin and one of the driven electrode 110, the reference electrode 120, and the sense electrode 131, broadcasting an electrode adjustment prompt to an external device.

9.1 Push Notifications

In one implementation, the EEG headset 102 also includes a wireless communication module 162, as shown in FIG. 3, configured to communicate wirelessly (e.g., directly or through a network, such as through the Internet or over a cellular network) with a smartphone, tablet, smartwatch, or other external wireless-enabled device carried or accessible by a nurse, doctor, therapist, epileptologist, or other EEG test administrator administering an EEG test with the EEG headset 102 to the user. Before initiating an EEG test, the wireless communication module 162 can connect wirelessly to an external device and can maintain a persistent wireless connection with the external device during the EEG test. During the EEG test, the controller 160 can push notifications for contact loss events, as described below, to the external device substantially in real-time in order to prompt the EEG test administrator to quickly correct electrode contact issues. For example, the controller 160 can push a notification in the form of a SMS text message or an in-application notification to the external device.

Figure 6:
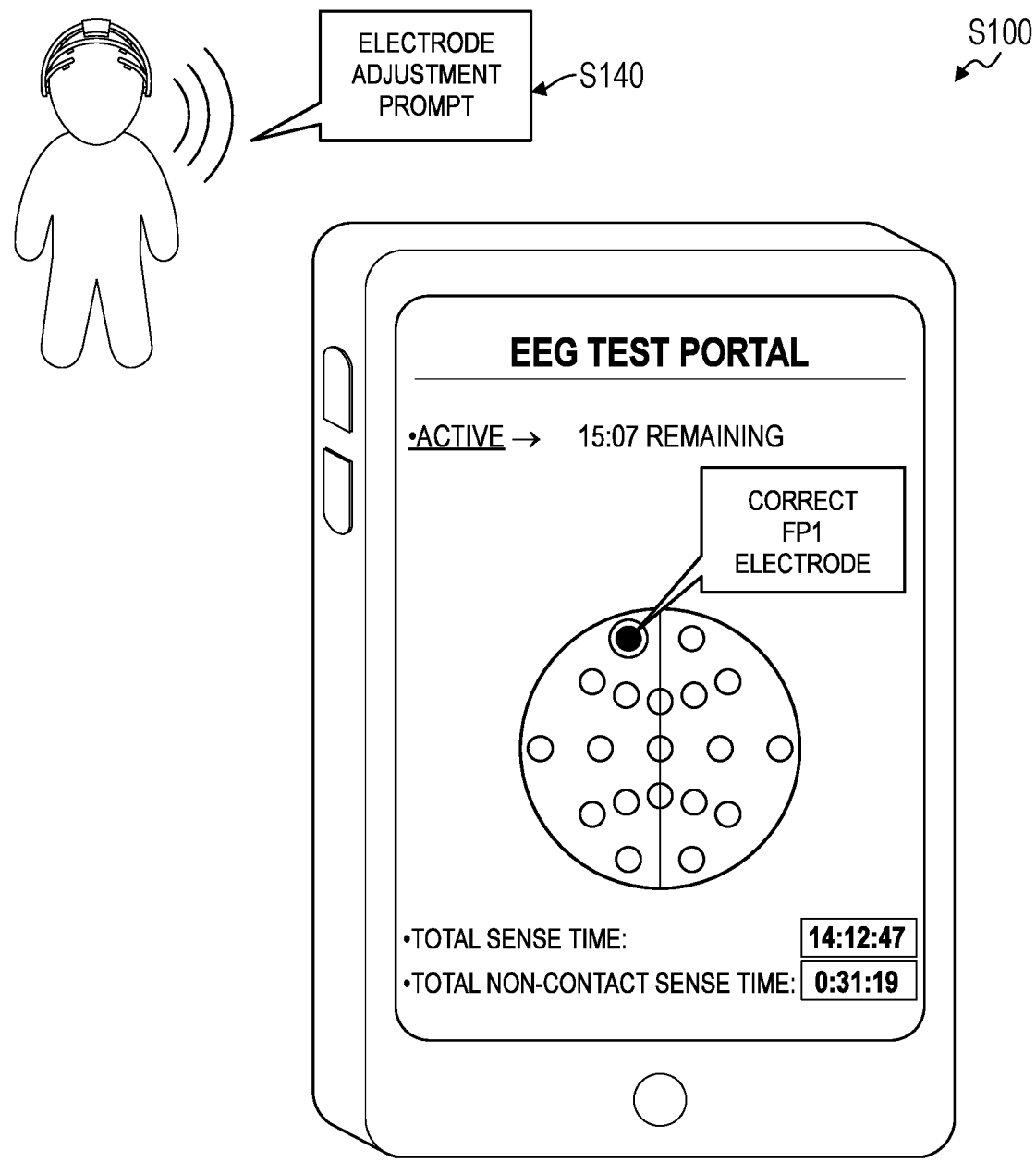
FIG. 6 is a flowchart representation of one variation of the method.

The external device can additionally or alternatively execute a native EEG test application including a virtual graphical representation of the EEG headset 102 and the drive, reference, and sense electrodes. In this implementation shown in FIG. 6, the controller 160 can push electrode status updates to the external device—such as via a short-range wireless communication protocol—substantially in real-time or in response to a change in the contact status of an electrode. Upon receipt of an update from the EEG headset 102, the native EEG test application can update the virtual graphical representation of the EEG headset 102 accordingly in order to visually indicate the contact status of each electrode. The native EEG test application can then serve audible, visual, and/or haptic prompts to the EEG test administrator to correct fitment of a particular electrode on the user's scalp when a predefined trigger event is detected, as described below.

The controller 160 can therefore selectively push notifications to the external device in response to detected contact loss events in Blocks S122, S124, and S132. Alternatively, the native EEG test application executing on the external computing device can regularly pull contact states of electrodes in the EEG headset 102, such as once per second or once per five-second interval, and implement methods and techniques described above and below to selectively serve prompts to the EEG test administrator to correct skin contact at one or more electrodes in the EEG headset 102.

9.2 Electrode Adjustment Prompt

In one implementation, in response to a contact loss event, the controller 160 generates a notification that: identifies a specific electrode that has lost contact with the user's skin; includes an identifier of the EEG headset 102 worn by the user; and includes a textual and/or graphical prompt to restore proper contact between the user's skin and the identified electrode by adjusting the EEG headset 102. For example, if the driven electrode 110 is determined to be in improper contact with the user's skin in Block S124, the controller 160 can generate a notification including a graphical representation of the EEG headset 102 including the electrodes, can highlight the driven electrode 110 (e.g., in red) in the graphical representation of the EEG headset 102, and can overlay a textual prompt reciting "Please depress the driven electrode 110 on the right side of the patient's neck until proper body contact is restored" over the graphical representation of the EEG headset 102.

In another implementation, the controller 160 can: generate an electronic notification containing a prompt to correct contact between a particular electrode—in the set of electrodes—determined to be out of contact with the user's skin (or out of contact with the user's skin for more than a threshold period of time); insert a virtual map of locations of the set electrodes in the EEG headset 102 into the electronic notification; and indicate the particular electrode within the virtual map in Block S140. For example, if a Fp1 sense electrode 131 is determined to be in improper contact with the user's skin in Block S132, the controller 160 can: generate a notification including a graphical representation of the EEG headset 102 representing general positions of electrodes; highlight the Fp1 electrode (e.g., in red) in the graphical representation of the EEG headset 102; and insert a textual prompt reciting "Please tighten the front adjustable headband on the headset until contact at the Fp1 electrode is restored" over the graphical representation of the EEG headset 102 in Block S140.

In a similar implementation, each electrode in the EEG headset 102 can be color-coded (or patterned) with a color (e.g., or pattern) unique within the set of electrodes, and, in response to a contact loss event at a particular electrode, the controller 160 can generate a contact loss notification identifying the particular electrode by its unique color (or pattern). However, the controller 160 and/or the external device can implement any other method or technique to notify an EEG test administrator of a contact loss event.

9.3 Notification Timing

In this implementation, the controller 160 can also delay transmission of a notification of a contact loss event at a particular electrode until the particular electrode has been out of proper contact with the user's skin for at least a threshold duration, a custom duration selected by the EEG test administrator, or a duration proportional to the physical distance between the user and the EEG test administrator. For example, the controller 160 can track a duration of a contiguous period of time during which a first sense electrode 131 is determined to be in improper contact with the user's skin; and then transmit an electronic notification prompting adjustment of the first sense electrode 131 to an external device accessible by an electroencephalography test administrator if the duration of the contiguous period of time exceeds a threshold duration, such as five seconds. In a similar example, the controller 160 can track a total duration of time over which the first sense electrode 131 is determined to be in improper contact with the user's skin since a last manual adjustment of the EEG headset 102 or within a preset interval (e.g., one minute, five minutes); and then transmit an electronic notification prompting adjustment of the first sense electrode 131 to the external device in Block S140 if the total duration of time exceeds a threshold duration, such as twenty seconds since the EEG headset 102 was last adjusted by the EEG test administrator or ten seconds within a last one-minute interval.

In another example, the controller 160 can track a total duration of time during which sense electrodes across the set of sense electrodes 130 are determined to be in improper contact with the user's skin (i.e., a sum of the total time that each sense electrode 131 has been out of contact with the user's skin), such as since a last manual adjustment of the EEG headset 102 or within a preset interval; and then transmit, to the external device, a second electronic notification prompting restart of the current EEG test substantially in real-time when this total duration of time exceeds a second threshold duration (e.g., one minute, one minute within the last five minutes, or 5% of the total sensed time across the set of sense electrodes). (In a similar example, the controller 160 can determine asynchronously that insufficient data was collected through electrodes during the EEG test, such as if the ratio of total time that a sense electrode 131 was in improper contact with the user's skin to the total recorded data stream time across 19 sense electrodes exceeds 5%, and then prompt the EEG test administrator to repeat the EEG test following its conclusion.) The controller 160 can therefore selectively push a notification to an EEG test administrator (e.g., to a smartphone carried by the EEG test administrator or to another external device accessible to the EEG test administrator) when an amount of time that a single sense electrode 131 has been out of contact with the user's skin or when a total amount of time that sense electrodes in the set have been out of contact with the user's skin exceeds a preset threshold time.

The controller 160 can implement similar methods and techniques to push such a notification to the EEG test administrator if either the driven electrode 110 or the reference electrode 120 is determined to be out of contact with the user's skin. For example, because improper contact between the user's skin and either the driven electrode 110 or the reference electrode 120 may produce raw (or composite) sense signals that are unusable, the controller 160 can implement shorter threshold times to trigger transmission of an electrode adjustment prompt to the EEG test administrator following detection of improper skin contact at the drive and sense electrodes, such as: a contiguous two seconds of improper contact; five seconds of improper contact since a last manual adjustment of the EEG headset 102; or five seconds within a five minute interval.

9.4 Filtered Notifications

In a similar variation, the controller 160 responds to contact loss events by selectively pushing notifications to the EEG test administrator. In this variation, the controller 160 can withhold contact loss notifications from an EEG test administrator based on a type of electrode that has lost contact, a total number of electrodes not in proper contact at a particular instant in time, a total duration of time that one or a group of electrodes have been in improper contact with the user's skin (as described above), and/or a type of EEG test being administered to the user, etc.

In one implementation, for a general EEG test in which the EEG headset 102 is configured to record data from all channels (e.g., all 19 electrodes in a 10-20 headset configuration) in the EEG headset 102, the controller 160 can push contact loss notifications to an EEG test administrator substantially in real-time if either the driven electrode 110 or the reference electrode 120 is determined to have lost contact with the user's skin. However, the controller 160 can delay notifying the EEG test administrator of contact loss events at sense electrodes until a total number of sense electrodes simultaneously not in contact with the user's skin surpasses a threshold electrode count (e.g., two electrodes, three electrodes). In one example, the controller 160 can implement a static, preset threshold electrode count, or the threshold electrode count can be customized by the EEG test administrator, such as through the native EEG test application executing on an external device, such as a smartphone or tablet carried by the EEG test administrator. In another example, the controller 160 can dynamically adjust the threshold number of electrodes based on a physical distance between the EEG headset 102 and the external device. In this example, the controller 160 and the wireless communication module 162 can cooperate to implement time-of-flight techniques to estimate the distance between the EEG headset 102 and the external device, and the controller 160 can adjust the threshold electrode count—to trigger prompting the EEG test administrator to correct a position of the EEG headset 102—proportional to this determined distance. In this example, the controller 160 can set the threshold electrode count to: null (i.e., zero electrodes) for a distance of less than five feet between the EEG headset 102 and the external device; one electrode for a distance of five feet to ten feet between the EEG headset 102 and the external device; two electrodes for a distance of ten feet to thirty feet between the EEG headset 102 and the external device; three electrodes for a distance greater than thirty feet between the EEG headset 102 and the external device.

During execution of the EEG test at the EEG headset 102, the controller 160 can implement definitions of "active" sense electrodes noted in the EEG test parameters to selectively filter contact loss events and to selectively issue notifications to the EEG test administrator (or to the user, etc.) to correct contact between these active sense electrodes and the user's skin. In particular, the controller 160 can: generate a prompt specifying adjustment of a first sense electrode 131 defined as relevant (or "active") for a type of the electroencephalography test currently underway at the EEG headset 102 in response to determination of improper contact between the user's skin and the first sense electrode 131 and then serve this prompt to the EEG test administrator, as described above; while also disregarding determination of improper contact between the user's skin and a second sense electrode 132 defined as irrelevant (or "inactive") for the type of electroencephalography test currently underway at the EEG headset 102.

Alternatively, the controller 160 can set the signal processor 150 to deactivate (e.g., "ignore") sense channels for sense electrodes designated as inactive (or not designated as active) during the EEG test; the signal processor 150 can therefore not test inactive sense electrodes for proper skin contact during the EEG test.

Yet alternatively, the signal processor 150 can continue to process sense signals from the inactive sense electrodes and predict future contact states at active sense electrodes based on determined skin contact states at inactive sense electrodes. For example, poor contact at an Fp1 electrode in a 19-sense-electrode EEG headset 102 may be indicative of poor skin contact—in the near future—at the Fp2 electrode (and vice versa). In this example, when executing a right-frontal-lobe EEG test in which sense signals from the Fp2, F4, and F8 electrodes are recorded exclusively, the controller 160 can preempt contact loss at the Fp2 by prompting the EEG test administrator to check the Fp2 electrode if poor contact is detected at the Fp1 electrode, such as despite determination that the Fp2 electrode is currently in proper contact with the user's skin. In this implementation, the controller 160 (or the native EEG test application described above), can thus implement a virtual model of a mechanical structure of the EEG headset 102 and/or a model or lookup table defining relationships between contact loss events at electrodes across the EEG headset 102 to predict future contact loss events at active electrodes based on contact states of inactive electrodes.

Similarly, when prompting the EEG test administrator to correct contact at a particular (active) electrode due to contact loss at the particular electrode, the controller 160 can also prompt the EEG test administrator to check other (active) electrodes—currently determined to be in proper contact but that have historically exhibited contact loss concurrently with contact loss at the particular electrode (e.g., as defined in the virtual model of the EEG headset 102)—for proper contact when correcting the particular electrode.

Yet alternatively, the signal processor 150 can process (raw or composite) sense signals from all sense electrodes and issue flags for contact loss events for all sense electrodes, and the controller 160 can generate and transmit notifications for contact loss events at only the active sense electrodes and discard (e.g., ignore) contact loss events for inactive sense electrodes. However, the signal processor 150 and the controller 160 can cooperate in any other way to selectively activate and deactivate sense electrodes (or sense channels) and to selectively issue notifications for contact loss events at active sense electrodes during an EEG test. The native EEG test application can similarly selectively update a graphical representation of the EEG headset 102 to indicate contact states or contact loss events at active electrodes only and can selectively serve relevant prompts to the EEG test administrator (or to the user directly, as described below).

9.5 Adjustment Directives

In another variation, in Block S140, the controller 160 populates a prompt to correct skin contact at a particular electrode with a description of a preferred or suggested mode of correction at the particular electrode. In one implementation, in response to detection of improper contact between a first sense electrode 131 and the user's skin, the controller 160: predicts an adjustment mode for the EEG headset 102 to improve contact between the first sense electrode 131 and the user's skin based on a virtual model of a mechanical structure of the EEG headset 102; inserts a description of the adjustment mode into an electronic notification; and transmits the electronic notification to a local computing device.

In one example in which the EEG headset 102 includes a lower-rear headband supporting T3, T5, O1, O2, T6, and T4 electrodes, if the signal processor 150 determines that at least three of these six electrodes on the lower-rear headband are in improper contact at a particular instant in time or are exhibiting fluctuating contact states, the controller 160 can: predict that the lower-rear headband is loose on the user's head based on a virtual model of a mechanical structure of the EEG headset 102, as described above; insert a prompt to tighten the lower-rear headband into an electronic notification; and then transmit the electronic notification to the external device for response by the EEG test administrator. In a similar example, the EEG headset 102 includes: a lower-rear headband supporting T3, T5, O1, O2, T6, and T4 electrodes; a lower-front headband supporting F7, Fp1, Fp2, and F8 electrodes; a center headband supporting C3, CZ, and C4 electrodes; and a center-front headband supporting F3, FZ, and F4 electrodes. In this example, if the signal processor 150 determines that at least one of the C3, CZ, and C4 electrodes and at least one of the F3, FZ, and F4 electrodes are in improper contact at a particular instant in time or are exhibiting fluctuating contact states, the controller 160 can: predict that either the lower-rear headband or the front-lower headband is too tight on the user's head; insert a prompt to loosen the lower-rear and lower-front headbands into an electronic notification; and then transmit the electronic notification to the external device for response by the EEG test administrator.

In another example, the controller 160 can access a set of template images of contact states across electrodes in a like EEG headset 102, wherein each template image defines a (unique) combination of electrodes in proper and improper contact and is associated with a particular adjustment mode to correct electrodes in improper contact. In this example, the controller 160 can match an image of current contact states across electrodes in the EEG headset 102 to a particular template image, insert a description of the adjustment mode stored with the matched template image into an electronic notification, and then serve this notification to the EEG test administrator.

The controller 160 can thus implement: a virtual model of a mechanical structure of the EEG headset 102; a model or lookup table defining relationships between contact states of groups of electrodes and adjustment of the support structure of the EEG headset 102; or a statistical model or table of common causes of contact loss events of specific electrodes; etc. to predict adjustment modes that will correct loss of skin contact at one or more electrodes in the EEG headset 102 and then serve an electrode adjustment prompt containing a description of this adjustment mode to the EEG test administrator in order to streamline and guide manual adjustment of the EEG headset 102 in real-time during an EEG test. However, the controller 160 (or the native EEG test application, etc.) can implement any other method or technique to transform the contact states of one or more electrodes in the EEG headset 102 into a directed prompt to correct skin contact at these electrodes.

The controller 160 can also implement tiered adjustment modes when serving guidance to the EEG test administrator for correct skin contact at an electrode. For example, for the reference electrode 120 determined to be in poor contact with the user's skin (e.g., the user's right earlobe or the right side of the user's neck), the controller 160 can sequentially serve guidance to the EEG test administrator to: jostle the reference electrode 120; then clean the user's skin at the location of the reference electrode 120 if poor skin contact persists after jostling; then exchange a disk-shaped electrode tip for a bristle electrode tip at the reference electrode 120 if poor skin contact persists after cleaning; and finally to replace the reference electrode 120 entirely if poor skin contact persists after exchanging electrode tips. In this example, the controller 160 can receive confirmation from the EEG test administrator that such guidance was followed and attempted, such as through the native EEG test application and sequentially step through such preplanned adjustment modes specific to the reference electrode 120 (or generic to all electrodes in the EEG headset 102). The controller 160 can also transmit updated notifications or electrode contact states to the external device for presentation to the EEG test administrator substantially in real-time. The controller 160 can additionally or alternatively update lighted indicators (described below) integrated into the headset to visually indicate contact states of the electrodes substantially in real-time. However, the controller 160 can serve any other guided and/or tiered prompts to the EEG test administrator (or to the user directly) in any other suitable way in Block S140.

9.6 Integrated Contact Quality Indicator

In one variation, the EEG headset 102 further includes a lighted indicator 164 adjacent each electrode and updates a state of each lighted indicator 164 according to the contact state of its corresponding electrode. For example, each electrode can include a red (i.e., single-color) LED opposite its set of prongs and electrically coupled to a corresponding LED driver within the controller 160. In this example, the controller 160 can activate (i.e., turn ON) an LED in a particular electrode when the particular electrode is determined to have lost contact with the user's skin in Block S122, S124, or S132. In another example, each electrode can include a multi-color LED opposite its set of prongs; for each electrode in the EEG headset 102, the controller 160 can set the color of an LED on an electrode: to green if contact between the user's skin and the electrode is determined to be proper; to red if contact between the user's skin and the electrode is determined to be improper; and to yellow if contact between the user's skin and the electrode is fluctuating between proper and improper (e.g., at a rate between 0.1 Hz and 2 Hz). In a similar example, each electrode can include a discrete red LED and a discrete, adjacent green LED opposite its set of prongs; for each electrode in the EEG headset 102, the controller 160 can activate either the red LED or the green LED based on the skin contact state of the electrode.

In this variation, in Block S140, the controller 160 can: illuminate a first lighted indicator—arranged in the EEG headset 102 adjacent the first sense electrode 131—in a first color to indicate improper contact between the user's skin and the first sense electrode 131 in response to determination of improper contact between the user's skin and the first sense electrode 131 in Block S132; and can illuminate a second lighted indicator—arranged in the EEG headset 102 adjacent the second sense electrode 132—in a second color to indicate proper contact between the user's skin and the second sense electrode 132 in response to determination of proper contact between the user's skin and the second sense electrode 132 in Block S136. The controller 160 can thus selectively illuminate lighted indicators 164 integrated into the EEG headset 102 adjacent electrodes determined to be in poor contact with the user's skin in order to visually indicate to the EEG test administrator—directly on the EEG headset 102—which electrodes require adjustment, such as in addition to transmitting an electrode adjustment prompt to the external device associated with the EEG test administrator. (The controller 160 can also selectively change colors of or selectively adjust illumination patterns (e.g., blinking patterns) of these lighted indicators 164 to indicate their contact states.) The controller 160 can similarly visually communicate to the user wearing the EEG headset 102—such as while sitting before a mirror—which electrodes require correction, and the user can depress regions of the support structure near illuminated lighted indicators 164 (or red or blinking lighted indicators) directly to correct skin contact at these electrodes.

In the foregoing implementations, when lighted indicator 164 (e.g., an LED) adjacent an electrode is activated, electromagnetic radiation output by the lighted indicator 164 may produce an extraphysiologic artifact in the signal output by its corresponding (i.e., adjacent) electrode. However, the reference and sense signals collected by the reference and sense electrodes, respectively may include substantially similar indicator-based extraphysiologic artifacts, which may be exclude from each composite sense signal via common-mode rejection when the raw reference signal is subtracted from raw sense signals at the signal processor 150 in Block S131, as described above.

However, the controller 160 can modify a state of any other one or more lighted indicators 164 integrated into the EEG headset 102 in order to visually indicate the contact state or contact quality of each electrode on the user's skin.

9.7 User-Directed Notifications

In one variation, the controller 160 (or a native EEG test application executing on a computing device carried by or accessible to the user) can also serve a prompt to correct skin contact at an electrode directly to the user. For example, the controller 160 (or the native EEG test application) can implement methods and techniques described above to update a lighted indicator integrated into the EEG headset 102 to indicate poor contact at a particular electrode adjacent the lighted indicator and then push a prompt to correct the particular electrode to the user's smartphone, such as by depressing the particular electrode or by adjusting a headband supporting the particular electrode on the user's head. While looking at a mirror, the user can thus adjust the particular electrode accordingly. The controller 160 can thus serve a prompt directly to the user in order to reduce a burden on the EEG test administrator to monitor the user or if the user is completing an EEG test without the aid of an EEG test administrator (e.g., while at home).

The controller 160 can also selectively serve electrode adjustment prompts to one of the user and the EEG test administrator based on a type of adjustment needed. For example, the controller 160 can serve prompts to correct electrodes exhibiting moderate contact quality—such as characterized by contact quality oscillating between proper and improper and improper for no more than ten seconds per twenty-second interval—to the user. In this example, the user can thus manually depress such an electrode with her finger to correct contact with the user's skin. However, in this example, the controller 160 can serve prompts to correct electrodes exhibiting poor contact quality—such as characterized by improper contact for more than ten seconds per twenty-second interval—exclusively to the EEG test administrator, as such poor contact quality may require the EEG test administrator to clean the user's skin or replace an electrode tip.

However, the controller 160 (or native EEG test application) can implement any other method or technique to serve electrode adjustment prompts directly to the user.

9.8 Contact Loss Checks

In one variation, the EEG headset 102 checks an electrode previously determined to have lost contact with the user's skin to confirm whether contact has been reestablished.

In one implementation, the signal processor 150 deactivates a particular electrode: in response to detecting that this particular electrode has lost contact with the user's skin in Block S122 or S134; in response to the corresponding (raw or digital) sense signal differing from an average amplitude of all sensor signals by a threshold proportion (e.g., 100%) during the current sampling period; or in response to the average amplitude of the corresponding (raw or digital) sense signal approaching either voltage rail of the EEG headset 102 (e.g., 0V and $V_{cc}$). In this implementation, the signal processor 150 intermittently reactivates that particular electrode, reads a sense signal from the particular electrode, and analyzes the sense signal according to Block S134 to determine whether a particular electrode has regained contact, such as on a regular interval of one per second or once per five-second interval. Thus, if the signal processor 150 determines that proper contact between the particular electrode and the user's skin has returned, the signal processor 150 can reactivate the particular electrode; otherwise, the signal processor 150 can return the particular electrode to the inactive state. While the particular electrode is in the inactive state, the signal processor 150 can continue to sample the particular electrode but discard this sense signal; alternatively, the signal processor can deactivate the particular electrode by electrically decoupling the particular electrode from the ADC or by otherwise isolating the particular electrode from other sense electrodes in the EEG headset 102. Furthermore, while the particular electrode is deactivated, the signal processor 150 can refrain from recording the corresponding sense signal from the digital file in Block S150, refrain from incorporating the corresponding sense signal from calculation of a virtual reference signal in Block S121, and/or refrain from incorporating the corresponding sense signal from calculation of a DC component of the drive signal in Block S162 as described below. However, once proper contact between the particular electrode and the user's skin is reestablished, the signal processor 150 can return to recording the corresponding sense signal in Block S150, incorporating the corresponding sense signal into calculation of the virtual reference signal in Block S121, and/or incorporate the corresponding sense signal into calculation of the DC component of the drive signal in Block S162. For example, if the signal processor 150 determines that a first sense electrode has lost contact with the user's skin at a first time, the signal processor 150 can then: reactivate the first sense electrode at a second time succeeding the first time by a preset check duration (e.g., on a five-second interval); read a sense signal from the first sense electrode; determine that the first electrode is in proper contact with the user's skin at the second time if the sense signal includes a signal component oscillating at the reference frequency; and maintain the first electrode in an active state following the second time if the first electrode is in proper contact with the user's skin.

The EEG headset 102 can additionally or alternatively implement the foregoing methods and techniques in response to receipt of confirmation from the EEG test administrator (or from the user) that a particular electrode has been adjusted following transmission of an electrode adjustment prompt specifying adjustment of the particular electrode. For example, the EEG test administrator can confirm response to an electrode adjustment prompt through an instance of the native EEG test application executing on her mobile computing device; the native EEG test application can wirelessly transmit this confirmation to the EEG headset 102; upon receipt of this confirmation, the signal processor 150 can implement the foregoing methods and techniques to retest this sense electrode. The controller 160 can then serve a notification to the EEG test administrator confirming proper adjustment of the particular electrode or prompting further adjustment if the controller 160 determines that the particular electrode is still exhibiting poor contact with the user's scalp.

However, the EEG headset 102 can respond to loss of contact between an electrode and the user's skin in any other way and retest this contact in response to any other event or trigger.

9.9 Warnings

Figure 8:
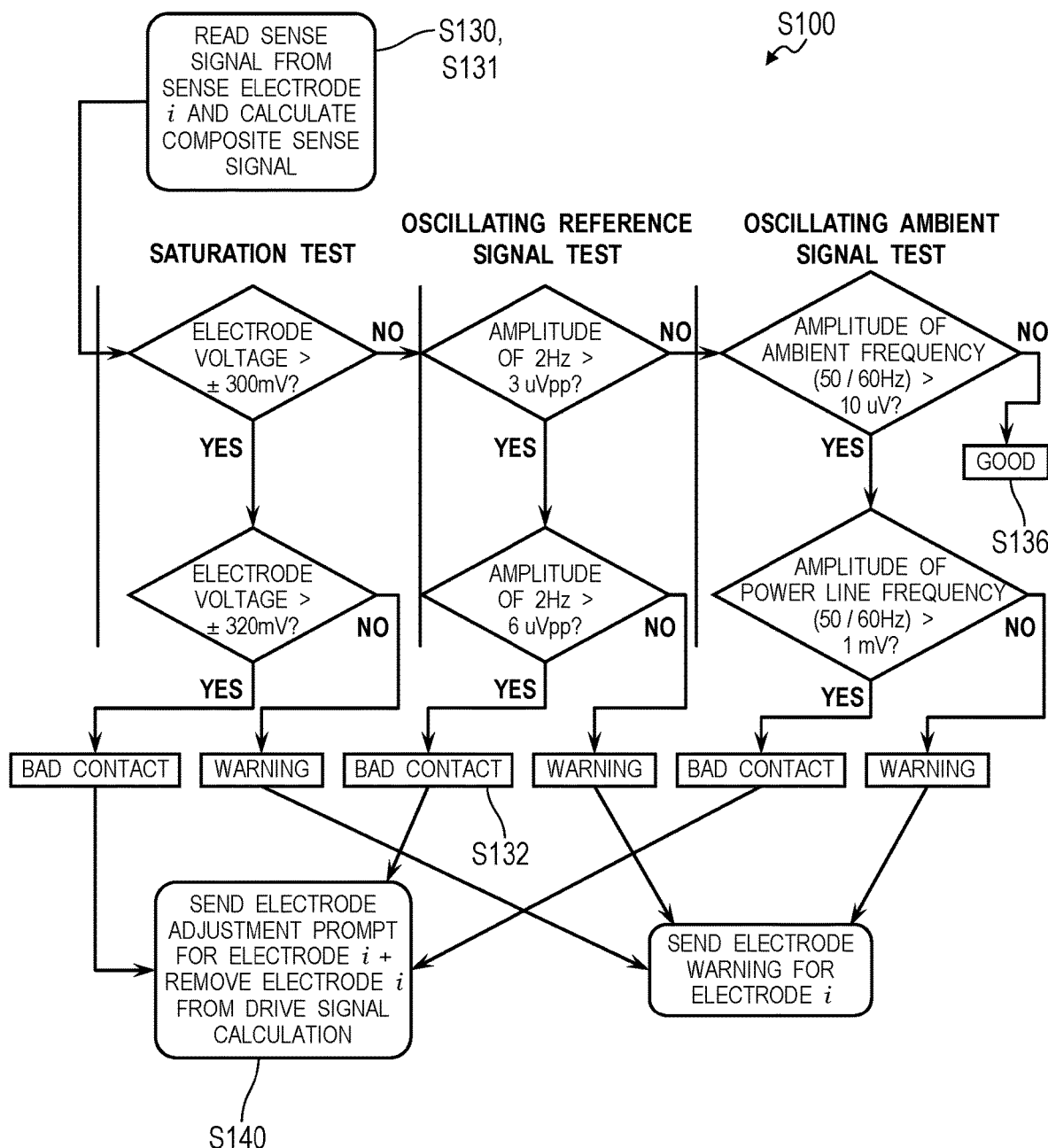
FIG. 8 is a flowchart representation of one variation of the method.

In one variation shown in FIG. 8, the controller implements additional checks to determine whether a sense electrode is in proper contact with the user's skin (e.g., exhibiting strong capacitive coupling to the user's scalp), in poor contact with the user's skin (e.g., exhibiting poor capacitive coupling to the user's scalp), or not in contact with the user's skin (e.g., exhibiting no detectable capacitive coupling to the user's scalp) and can serve notifications to the EEG test administrator accordingly. For example and as shown in FIG. 8, the controller can read a composite digital sense signal originating from a sense electrode in Block S130 and then determine that the sense electrodes is nearing saturation if the composite digital sense signal approaches a saturation voltage (e.g., exceeds 300 mV for a saturation voltage of 320 mV). If the sense electrode is nearing saturation but is not saturated, the controller 160 can issue a warning for the sense electrode; if the sense electrode is saturated, the controller 160 can flag the sense channel, issue a prompt to correct the sense electrode, and/or discard the composite digital sense signal for this sampling period.

However, if the sense electrode is not saturated, the controller 160 can then check whether the composite digital sense signal contains a component oscillating at the reference frequency (e.g., 2 Hz). In particular, because the reference signal is subtracted from the sense signal to produce the composite digital sense signal, the composite digital sense signal may exclude this oscillating reference component if both the sense and reference electrodes are in proper contact with the user's skin. Therefore, if the controller 160 determines that the component in the composite digital sense signal oscillating at the reference frequency exhibits a peak-to-peak voltage greater than a low threshold reference voltage (e.g., 3 uVpp) but less than a high threshold reference voltage (e.g., 6 uVpp), the controller 160 can issue a warning that the sense electrode may be in poor contact or losing contact with the user's skin. Similarly, if the controller 160 determines that the component in the composite digital sense signal oscillating at the reference frequency exhibits a peak-to-peak voltage greater than the high threshold reference voltage, the controller 160 can flag the sense channel, issue a prompt to correct the sense electrode, and/or discard the composite digital sense signal for this sampling period.

However, if this oscillating component of the composite digital sense signal is characterized by a peak-to-peak voltage less than the low threshold ambient voltage, the controller can then check whether the composite digital sense signal contains a component oscillating at the ambient frequency (e.g., 60 Hz). In particular, because the reference signal is subtracted from the sense signal to produce the composite digital sense signal, the composite digital sense signal may exclude this oscillating ambient component if both the sense and reference electrodes are in proper contact with the user's skin. Therefore, if the controller 160 determines that the component in the composite digital sense signal oscillating at the ambient frequency exhibits a peak-to-peak voltage greater than a low threshold ambient voltage (e.g., 10 uVpp) but less than a high threshold ambient voltage (e.g., 100 uVpp), the controller 160 can issue a warning that the sense electrode may be in poor contact or losing contact with the user's skin. (In particular, because amplitude of the oscillating ambient component in the sense and reference signals may vary more widely as a function of capacitive coupling between the user and electrical components and power lines in the user's vicinity, the controller 160 can implement a wider tolerance for detecting proper and improper sense electrode contact from peak-to-peak voltage component oscillating at the ambient frequency in the composite digital sense signal.) Similarly, if the controller 160 determines that the component in the composite digital sense signal oscillating at the ambient frequency exhibits a peak-to-peak voltage greater than the high threshold ambient voltage, the controller 160 can flag the sense channel, issue a prompt to correct the sense electrode, and/or discard the composite digital sense signal for this sampling period.

The controller 160 can then selectively serve a warning or an electrode adjustment prompt to the EEG test administrator overseeing the EEG test in Block S140 based on contact quality between the sense electrode and the user's skin. The controller 160 can also selectively flag, annotate, and/or disable recordation of the composite digital sense signal read from this sense electrode based on such contact quality, as described below.

10. Setup

In one variation, the controller 160 (and/or the native EEG test application executing on the external device) implements the foregoing methods and techniques to indicate to the EEG test administrator (or to the user) the contact state of each electrode substantially in real-time as the EEG headset 102 is placed on the user's head and adjusted in preparation for an EEG test. In this variation, the controller 160 can thus provide electrode contact feedback to the EEG test administrator substantially in real-time to enable the EEG test administrator to achieve proper contact between the user's skin and all electrodes in the EEG headset 102 before beginning the EEG test and moving physically away from the user, such as to prepare another user for another EEG test with a similar EEG headset 102.

In this variation, prior to installation of the EEG headset 102 on the user's head the controller 160 (or the native EEG test application, or a remote computer system) can also predict adjustments for the support structure (e.g., each headband) in the EEG in order to achieve proper skin contact across each electrode. For example, during setup, the EEG test administrator can enter the user's head shape and head side into the native EEG test application, such as through dropdown menus enumerating qualitative head shapes (e.g., square, round, diamond, triangular, oblong, and oval) and qualitative head sizes (small, medium, and large). The native EEG test application can then retrieve predefined setup instructions corresponding to the combination of head shape and head size entered by the EEG test administrator, such as a length or adjustment position of each headband within the EEG headset 102 to accommodate the user's head shape and size. The native EEG test application can then serve these instructions to the EEG test administrator through a display integrated into the device executing the native EEG test application.

In the foregoing example, during setup, the EEG test administrator can also enter the user's hair type, quality, and quantity into the native EEG test application, such as through dropdown menus enumerating qualitative hair types (e.g., none, straight, wavy, curly, kinky, and dreadlocks) qualitative hair thicknesses (e.g., thin, full, and thick); and qualitative hair quantity (none, bald above crown, buzz, short, moderate, or long). The native EEG test application can then retrieve predefined contact insert types for each electrode based on the user's hair type, quality, and quantity entered by the EEG test administrator, such as a callout for one of: an elastic bristle insert; a rigid prong insert; a flat contact disk insert; and a domed contact disk insert; etc. for each electrode. The native EEG test application can then serve these contact insert type callouts to the EEG test administrator through the device executing the native EEG test application.

Once the EEG headset 102 is placed on the user's head and adjusted to achieve proper skin contact across all electrodes in the EEG headset 102, as confirmed by the controller 160 in Blocks S126 and S136, the controller 160 (or the native EEG test application, or a remote computer system) can store headband adjustments and/or contact insert types for each electrode in an electronic profile for the user. For example, the remote computer system can store this configuration as a target configuration for the user in the user's electronic profile. If results of the subsequent EEG test indicate suitable skin contact across electrodes in the EEG headset 102, such as less than 5% improper contact across all electrodes for the entire duration of the EEG test, the remote computer system can also update this configuration for the user based on adjustments made to the EEG headset 102 or to contact insert types at each electrode during the EEG test to improve contact quality at each electrode. During setup of additional EEG tests in the future, the controller 160 (or the native EEG test application, or a remote computer system) can serve this headset configuration to an EEG test administrator tasked with configuring an EEG headset 102 for the user for these future EEG tests. Furthermore, during setup of additional EEG tests in the future, the controller 160 (or the native EEG test application, or a remote computer system) can serve suggestions—to the EEG test administrator—for taking special care in placing certain electrodes on the user based on poor contact quality at these electrodes during past EEG tests.

The controller 160 (or the native EEG test application) can implement similar methods and techniques to update a configuration of the EEG headset 102 for the user based on feedback provided manually by the EEG test administrator. For example, the EEG test administrator can enter—through the native EEG test application—various feedback, including: whether an adjustment suggested by the system resolved electrode contact issues; and/or types, directions, and/or degrees of adjustment made by the EEG test administrator to bring electrodes in the EEG into proper contact with the user's scalp. Based on these feedback, the native EEG test application can refine the stored EEG headset configuration for the user. The native EEG test application or remote computer system can also develop a generic model for predicting ideal configuration of the EEG headset for a population of users of head shape, age, hair style and length, etc. similar to that of the user based on feedback provided by the EEG test administrator.

The controller 160, native EEG test application, and/or remote computer system can therefore implement various learning algorithms to develop suggestions for improving contact between electrodes in the EEG headset 102 and scalps of users based on feedback supplied by EEG test administrators over time.

However, the controller 160 (or the native EEG test application, or a remote computer system) can feed data— collected during setup and execution of an EEG test at a user—forward to setup and execution of a later EEG test in any other way in order to reduce setup time for the later EEG test and/or to the quality of data collected during the later EEG test.

11. Signal Annotation

As shown in FIG. 1, one variation of the method S100 further includes Block S150, which recites: over a period of time, writing a digital representation of the first composite sense signal to a digital file; and annotating the digital representation of the first composite sense signal with contact states of the driven electrode 110, the reference electrode 120, and the first sense electrode 131 over the period of time. Generally, in Block S150, the controller 160 can record composite sense signals read from each sense electrode 131 to a digital file and can annotate each composite sense signal in the digital file with the contact states or contact state changes throughout the EEG test over which these composite sense signals were recorded. In particular, during operation (e.g., during an EEG test), the controller 160 can flag or annotate each sense channel (e.g., a data stream read from the reference electrode 120 and unique data streams generated from raw sense signals read from each sense electrode 131) with its contact status (e.g., a contact loss status and/or a proper contact status), such as for each sampling period or for each change in the contact state of the corresponding electrode.

In one implementation, the signal processor 150: reads a raw reference signal from the reference electrode or calculates a virtual raw reference signal from one or more sense electrodes; reads raw sense signals from sense electrodes in the EEG headset 102; and subtracts the (virtual) raw reference signal from each raw sense signal to calculate composite senses signals with noise removed. The controller 160 can then record each composite sense signal to the digital file (e.g., a digital electroencephalography test result file).

In this implementation, if the signal processor 150 determines that the reference electrode 120 or the driven electrode 110 has lost contact with the user's skin during a particular period of time during an EEG test in Block S122 or S124, the controller 160 can annotate a data stream read from each sense electrode 131 with a "discard" label, as these data streams are unreliable during this particular period due to lack of proper skin contact at the drive and reference electrode. In another example, in Block S132, if the signal processor 150 determines that 18 of 19 sense electrodes are in proper contact with the user's skin but that a $19^{th}$ sense electrode 131 has lost contact with the user's skin during a particular period of time during the EEG test, the controller 160 can annotate a data stream from the $19^{th}$ sense electrode 131 with a "contact lost" label to indicate that these data in the $19^{th}$ data stream are unreliable during this particular period.

Alternatively, in Block S150 the controller 160 can stream these data streams to a remote computer system, such as to the EEG test administrator's smartphone over wireless communication protocol, to a desktop computer connected to the EEG headset 102, or to a remote computer system (e.g., a remote server) over the Internet. The EEG test administrator's smartphone, the desktop computer connected to the EEG headset 102, or the remote computer system can then implement similar methods and techniques to store these data streams in a digital file and to associate these data streams with contact qualities of their corresponding electrodes.

12. Dynamic Drive Signal

As shown in FIG. 1, one variation of the method S100 includes: outputting a drive signal through a driven electrode 110 in Block S110, the drive signal including an alternating-current component oscillating at a reference frequency and a direct-current component; reading a reference signal from a reference electrode 120 in Block S120; in response to the raw reference signal including a first signal component oscillating at the reference frequency, confirming proper contact between the user's skin and the driven electrode 110 and between the user's skin and the reference electrode 120 in Block S126; reading a sense signal from each sense electrode 131 in a set of sense electrodes in Block S130; in response to each sense signal read from a first subset of sense electrodes in the set of sense electrodes at a first time including a third signal component oscillating at the reference frequency, confirming proper contact between the user's skin and the sense electrode 131 in Block S136. In this variation, the method S100 further includes: for each sense electrode 131 in the first subset of sense electrodes, calculating a composite sense signal by subtracting the raw reference signal from the analog sense signal output by the sense electrode 131 at the first time in Block S161; calculating a first combination of the first set of composite signals in Block S162; compiling (e.g., combining, summing) the first combination and a direct-current component of the drive signal at approximately the first time to calculate a second direct-current value for the drive signal in Block S163; and at a second time succeeding the first time, shifting the drive signal to the second direct-current value in Block S160.

In this variation, the method S100 can similarly include: outputting a drive signal through a driven electrode, the drive signal including an alternating-current component oscillating at a reference frequency and a direct-current component in Block S110; reading a set of sense signals from a set of sense electrodes at a first time in Block S120; calculating a first combination of the set of sense signals in Block S162; calculating a second direct-current value including a combination (e.g., a sum, an average, etc.) of the first combination and the direct-current component of the drive signal at approximately the first time in Block S163; and at a second time succeeding the first time, shifting the direct-current component of the drive signal output by the driven electrode to the second direct-current value in Block S160.

Generally, in Blocks S161, S162, S163, and S160, the controller 160 calculates a new DC component of the drive signal based on a combination of (raw or composite) sense signals read from each sense electrode 131 that is confirmed to be in proper contact with the user's skin during the current sampling period and then shifts the output voltage of the driven electrode to this new DC component during the next sampling period, thereby maintaining the center voltage of the drive signal at a center of the dynamic range of the system during the next sampling period, such as to compensate for the output voltage of a battery 170 or other power supply integrated into the EEG headset 102. The controller 160 can repeat this process throughout an EEG test, such as during each sampling period or during each time interval (e.g., one-second intervals) during the EEG test. In particular, the output voltage of the battery 170 (or other power supply) supplying power to the controller 160, the signal processor 150, and electrodes within the EEG headset 102 may dictate a dynamic range of the signal processor 150 (e.g., the dynamic range of the ADC). Furthermore, because the output voltage of the battery 170 may change as the battery 170 is discharged, as the temperature of the battery 170 changes, as the battery 170 ages, or as a load on the battery 170 changes, etc. over time, the dynamic range of the signal processor 150 may also change over time. Therefore, to ensure that raw reference and sense signals read by the signal processor 150 remain substantially centered within the dynamic range of the ADC over time, the controller 160 can recalculate the DC component of the drive signal over time. The signal generator 140 then modifies the drive signal dynamically during an EEG test according to the new DC component calculated by the controller 160. The controller 160 and the signal generator 140 can repeat this process at or after each sampling period during operation of the EEG headset 102.

In one implementation, at startup (e.g., at the beginning of an EEG test), the signal generator 140 generates a drive signal that includes a DC component at a voltage half of the nominal battery voltage. In one example in which the EEG headset 102 includes a battery configured to output a nominal 3.3V to the signal processor 150 and to amplifiers at each reference and sense electrode 131, at startup, the signal generator 140 can output a drive signal containing a 1.65V DC component to the driven electrode 110. For each subsequent sampling period, the controller 160 can: calculate a combination (e.g., a linear combination, an average) of composite digital sense signals read by the signal processor 150 (from which the raw reference signal read from the reference electrode 120 has already been subtracted in Block S131, as described above); transform the combination into a composite voltage value; and then combine this composite voltage value and the voltage of the DC component of the drive signal output during the current (or preceding) sampling period to calculate a new DC voltage for the drive signal at the next sampling period. The controller 160 can pass each new DC voltage of the drive signal to the signal generator 140, and the signal generator 140 can shift the drive signal to this new DC voltage during the next sampling period. The controller 160 can repeat this process to calculate a new DC voltage of the drive signal—approximately centered within the dynamic range of the system, as dictated by the nominal voltage of the battery 170—for each subsequent sampling period during operation of the EEG headset 102.

In the foregoing implementation, because signals read from sense electrodes determined to be in improper contact with the user's skin may be unreliable, the controller 160 can calculate the combination of composite digital sense signals originating exclusively from sense electrodes determined to be in proper contact with the user's skin during a current (or last) sampling period. The combination of these composite digital sense signals can thus represent the combined (e.g., average) voltage across sense electrodes in proper contact with the user's skin during the current (or last) sampling period, less the voltage of the reference signal during the current (or last) sampling period. By then combining (e.g., summing) a DC voltage represented by the combination with the DC voltage of the drive signal during the current (or last) sampling period, the controller 160 can calculate a new DC voltage—approximately aligned with the center voltage of the ADC—for the drive signal. The signal generator 140 can then shift the drive signal to this new DC voltage during the next sampling period in Block S160.

The controller 160 can repeat this process for each sampling period (or following a set of sampling periods). In particular, the controller 160 can track changes in skin contact quality at each electrode and dynamically adjust a subset of composite digital sense signals combined to calculate a composite (e.g., average) digital voltage value accordingly for each subsequent sampling period. For example, in Block S160, after updating the DC component of the drive signal at a first time, the controller 160 can determine improper contact between the user's skin and sense electrodes in a second subset of sense electrodes in Block S132 in response to each raw sense signal read from a second subset of sense electrodes in the set of sense electrodes at the first time excluding the third signal component oscillating at the reference frequency (or in response to each composite sense signal read from a second subset of sense electrodes in the set of sense electrodes at the first time including the third signal component oscillating at the reference frequency), wherein the second subset of sense electrodes is distinct from the first subset of sense electrodes.

In Block S160, the controller 160 can then: identify a second subset of sense electrodes in the set of sense electrodes in proper contact with the user's skin at the second time, the second subset of sense electrodes different from the first subset of sense electrodes; for each sense electrode 131 in the second subset of sense electrodes, calculate a voltage difference, in a second set of voltage differences, between a voltage of the raw reference signal and a voltage of a sense signal output by the sense electrode 131 at the second time; calculate a second combination of the second set of voltage differences; combine (e.g., sum, average) the second combination and a voltage of the direct-current component of the drive signal at approximately the second time to calculate a third direct-current voltage of the drive signal; and at a third time succeeding the second time, shift the direct-current component of the drive signal to the third direct-current voltage.

In particular, the signal processor 150 can continuously sample the sense electrodes. During each scan cycle, the controller can define a subset of sense electrodes in proper contact with the user's skin and then flag (raw or composite) sense signals read from each sense electrode in this subset of sense electrodes for calculation of the DC component of the drive signal output by the driven electrode in the next scan cycle.

Furthermore, when the driven electrode 110 and/or the reference electrode 120 are determined to have lost contact with the user's skin, the controller 160 can maintain a last DC component of the drive signal unchanged. In particular, in response to determination of improper contact between the user's skin and one of the driven electrode 110 and the reference electrode 120, the controller 160 can maintain the direct-current component of the drive signal substantially unchanged until proper contact between the user's skin and the driven electrode 110 and between the user's skin and the reference electrode 120 are confirmed.

Alternatively, in this variation, for the signal processor 150 that exhibits a dynamic range less than the nominal voltage output of the battery 170, at startup, the signal generator 140 can generate a drive signal that includes a DC component at a voltage (above the battery ground) half of the dynamic range of the signal processor 150. The controller 160 can then implement averaging techniques as described above to calculate a new drive signal DC voltage that centers the average outputs of the sense electrodes (and the reference electrode 120) for the current (or last) sampling period within the dynamic range of the signal processor 150.

For example, the controller 160 can: calculate a combination of composite digital sense signals read (from sense electrodes determined to be in proper contact with the user's skin) by the signal processor 150; combine (e.g., sum) this combination and a digital value representing the voltage of the DC component of the drive signal output during the current (or preceding) sampling period to calculate a composite (e.g., average) digital center signal value for the current sampling period. The controller 160 can then: calculate a digital difference by subtracting this composite digital center signal from the center of the dynamic range of the signal processor 150 (e.g., "127" for an 8-bit ADC outputting digital values between 0 and 255 in each sense channel); transform this digital difference value into a voltage difference; and add this voltage difference to the current (or last) DC voltage of the drive signal to calculate a new DC voltage for the drive signal at the next sampling period. The signal generator 140 can then implement this DC voltage accordingly at the next sampling period, as described above.

The signal generator 140 can therefore output a drive signal including a DC component that follows the sense signals (and the raw reference signal) collected by the sense electrodes (and by the reference electrode 120). The signal generator 140 can combine the dynamic DC component with a static AC component, such as a sinusoidal, 2.0 Hz, 17 millivolt peak-to-peak AC signal, as described above. However, the signal generator 140 can output a drive signal including DC and AC components at any other voltage and—for the AC component—oscillating at any other frequency and according to any other waveform. Furthermore, the controller 160 can implement the foregoing methods and techniques to process raw or composite analog sense signals to calculate a new DC component of the drive signal for each subsequent scan cycle.

13. Motion Tracking

In one variation, the EEG headset 102 further includes an accelerometer, gyroscope, compass, and/or other motion sensor, such as arranged in the housing described above. In this variation, the controller 160 can sample the motion sensor during operation (e.g., during an EEG test), correlate an output of the sensor with a magnitude and/or direction of motion of the user's head, and set an excess motion flag in response to the magnitude of motion of the user's head exceeding a threshold motion (e.g., acceleration) magnitude. The wireless communication module 162 can then push an excess motion notification to the external device substantially in real-time based on the excess motion flag. For example, the controller 160 can generate a notification including a textual prompt to quell the user, such as reciting, "The user is exceeding a motion limit for the current EEG test," and the wireless communication module 162 can push this notification to the external device, as described above, for substantially immediate response by the EEG test administrator. Based on the notification, the EEG test administrator can then return to and quiet the user.

Generally, movements by the user during the EEG test may create artifacts in the EEG data collected during the EEG test and/or may cause an electrode to lose contact with the user's skin. The EEG headset 102 can therefore sample the motion sensor during the EEG test, characterize the outputs of the motion sensor, and notify an EEG test administrator if the user's motion exceeds a motion limit, such as a motion limit characterized by relatively high risk of data artifacts or by relatively high risk of loss of electrode contact. The EEG headset 102 can therefore provide guidance to the EEG test administrator—through the external device or through an audible or visual indicator on the EEG headset 102—to minimize user motion that may create artifacts in EEG test data or lead to low-quality EEG data collected during the EEG test.

In one implementation, the EEG headset 102 includes an accelerometer, and the controller 160 retrieves acceleration limits for various motion types specified for an upcoming EEG test and generates excess motion notifications while the EEG test is in process based on these specified acceleration limits. For example, the controller 160 can access a database in which a maximum (X-, Y-, and Z-axis) composite acceleration for each of multiple motion types are specified for available EEG tests, including a walking-type motion characterized by accelerations below 0.5 Hz, a fidgeting motion characterized by accelerations between 0.5 Hz and 1.0 Hz, a talking-type motion characterized by accelerations between 1.0 Hz and 2.0 Hz, and a blinking-type motion characterized by accelerations greater than 2.0 Hz, etc. In this example, the database can define moderate acceleration limits for the walking-, fidgeting-, talking-, and blinking-type motions for a general seated EEG test, whereas the database can define relatively low acceleration limits for blinking-type motions for frontal lobe tests and relatively high acceleration limits for temporal lobe tests. Furthermore, in this example, for a general walking EEG test, the database can define a relatively high acceleration limit for walking-type motions and a relatively low acceleration limit for talking-type motions. The EEG headset 102 can therefore compare acceleration values output by the accelerometer to EEG test-specific motion limits to identify instances of excess motion, and the EEG headset 102 can generate and distribute notifications to the EEG test administrator (or directly to the user) accordingly.

Alternatively, the EEG headset 102 can implement generic motion limits across all EEG tests and can selectively activate and deactivate flags for excess motion types based on a type of the current EEG test. For example, when a general walking EEG test is underway, the EEG headset 102 can deactivate motion limits for walking-type and fidgeting-type motions but maintain motion limits for talking-type and blinking-type motions. However, in this example, when a seated frontal lobe test is underway, the EEG headset 102 can activate motion limits for all walking-, fidgeting-, talking-, and blinking-type motions.

The EEG headset 102 can additionally or alternatively notify the user directly of excess motion (and/or of electrode contact loss events, as described above), such as through a speaker integrated into the EEG headset 102 or through an external device (e.g., a smartphone, a tablet) carried or accessible directly by the user. However, the EEG headset 102 can implement any other method or technique to notify the EEG test administrator and/or the user of excess user motion and of electrode contact loss events. The EEG headset 102 can also annotate EEG data collected during the EEG test with motion data recorded through the motion sensor during the EEG test, such as by noting periods in each sense channel that corresponds in time to periods of overactivity or excessive motion by the user.

14. Active and Inactive Electrode Sets

Figure 7:
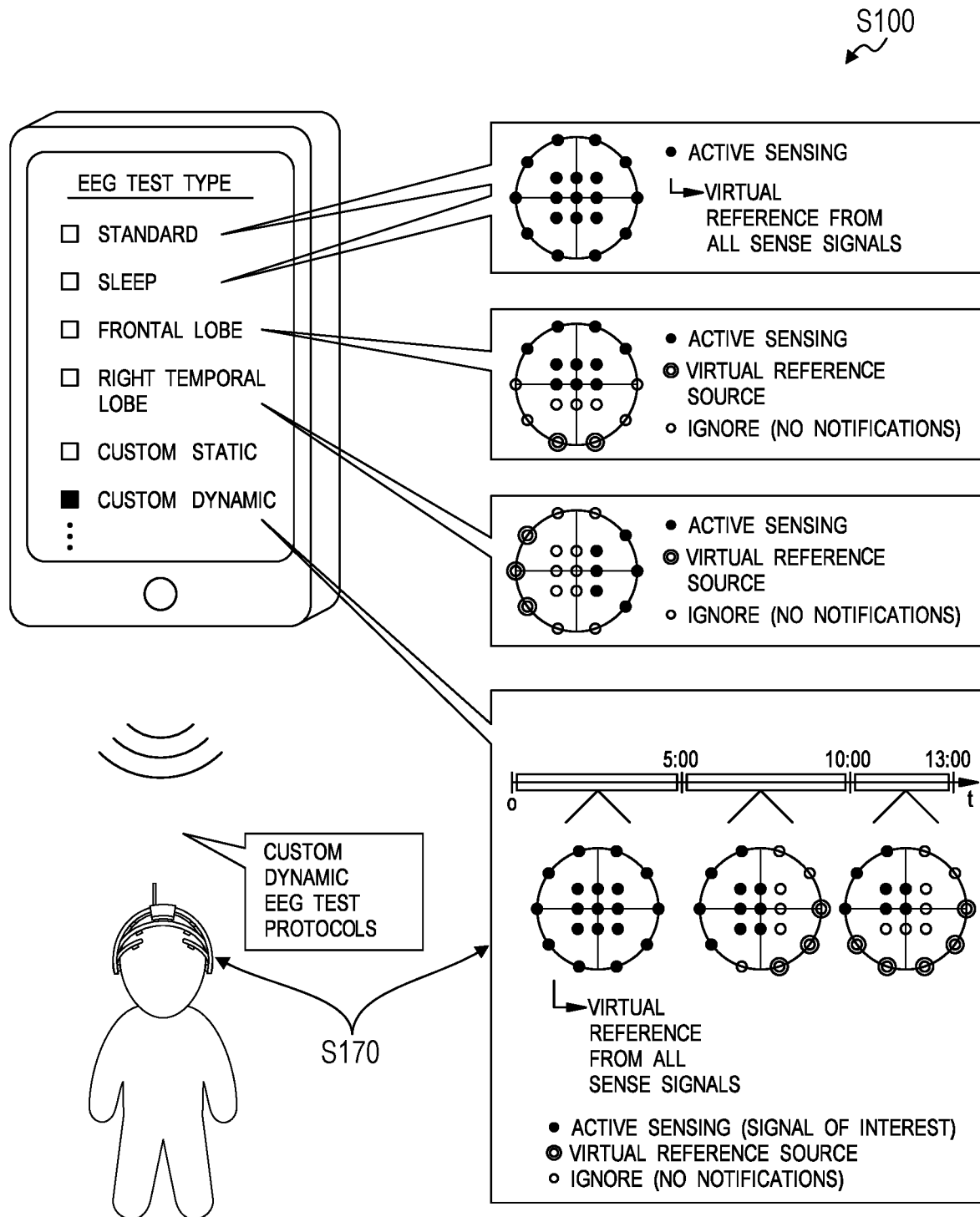
FIG. 7 is a flowchart representation of one variation of the method.

One variation of the method shown in FIGS. 2C and 7 includes Block S170, which recites selectively activating a first subset of sense electrodes in the EEG headset 102. In this variation, the EEG headset 102 can record sense signals from this first subset of sense electrodes to the digital file in Block S150 in order to limit file size and/or required bandwidth to transmit the digital file to another device without losing relevant or requested data. The EEG headset 102 can also track the DC component of the drive signal to a combination of sense signals read from the first subset of sense electrodes in Block S160 in order to center these sense signals within the dynamic range of these sense electrodes, thereby maintaining relatively high fidelity and limited "clipping" in these signals of interest. Furthermore, in this variation, the EEG headset 102 can selectively activate a second subset of sense electrodes—distinct from or overlapping the first subset of sense electrodes—and calculate a virtual reference signal from sense signals read from this second subset of sense electrodes in Block S121 in order to isolate the reference signal from signals of interest across the user's scalp, thereby maintaining high selectively to rejection of noise in composite sense signals written to the digital file in Block S150.

Therefore, in Block S170, the EEG headset 102 can execute Blocks of the method to selectively activate and deactivate sense electrodes, to selectively record sense signals corresponding to channels of interest, to selectively calculate virtual reference signals from multiple sense signals that may or may not correspond to channels of interest, and to dynamically adjust the DC component of the drive signal to follow sense signals corresponding to channels of interest, thereby rejecting noise in recorded signals while also limiting rejection of signals representative of local brain activity of interest.

Furthermore, by setting select sense electrodes as inactive during an EEG test, the controller 160 can: decrease power consumption thereby extending battery life of the EEG headset 102; and reduce measurement noise, such as less digital noise and power noise, thereby yielding higher-quality data for the channels of interests.

14.1 Active Electrode Selection

In one implementation, the native EEG test application—executing on the external device that is paired with the EEG headset 102—contains a list of selectable, preconfigured EEG test types, wherein each EEG test type specifies a test duration and defines a set of active sense electrodes corresponding to channels of interest (or located over an area of interest of a user's skull by EEG headset 102), as shown in FIG. 7. In this example, the native EEG test application can store a set of preconfigured EEG test types and parameters, including: a full EEG test type specifying a 40-minute duration with all 19 sense electrodes active (i.e., relevant to the full EEG test); a frontal lobe test type specifying a 20-minute duration with sense electrodes at the five frontal lobe positions (e.g., FZ, F3, F7, F4, and F8) and the two frontal polar sites (e.g., Fp1 and Fp2) active and all other sense electrodes inactive or allocated for calculation of a virtual reference signal; and a right-temporal lobe test type specifying a 15-minute duration and the two right-temporal lobe sense electrodes (e.g., T4 and T6) active and all other sense electrodes inactive; etc.

In another implementation, the native EEG test application can additionally or alternatively enable an EEG test administrator (or a neurologist, etc.) to design or configure a custom EEG test, such as a custom EEG test specifying a custom duration and a custom subset of occipital lobe, frontal lobe, parietal lobe, and/or center position sense electrodes as active, as shown in FIG. 7. Furthermore, the native EEG test application can enable the EEG test administrator (or a neurologist, etc.) to design or manually configure a dynamic EEG test in which a subset of active sense electrodes changes throughout the duration of the custom EEG test, such as based on time from start of the EEG test or based on artifacts or neural oscillations recorded during the EEG test.

Furthermore, through the native EEG test application, the EEG test administrator can select a standard EEG test from a pre-populated list of EEG tests, modify an existing EEG test, or configure a custom EEG test for an upcoming EEG test period. The external device executing the native EEG test application can then upload parameters of the selected or (re)configured EEG test to the EEG headset 102—such as in the form of identifiers or addresses of active sense electrodes and active time durations for each sense electrode)—such as over short-range wireless communication protocol in preparation for execution of a new EEG test by the EEG headset 102.

Upon selection of a set of channels of interest (or an area of interest on a user's scalp), the signal processor 150 can classify each sense electrode in the EEG headset 102 as one of: inactive (e.g., off and electrically isolated from the ADC); active and of interest (e.g., for outputting a sense signal that is recorded to a digital file and that is used to adjust the DC component of the drive signal); and active for virtual reference signal calculation (e.g., for outputting a sense signal exclusively for calculating a virtual reference). In particular, the signal processor 150 can label each sense electrode corresponding to a channel of interest as active and of interest and define a first subset of these sense electrodes. As described above, the signal processor 150 can also label a second subset of sense electrodes as active for virtual reference signal calculation, such as based on a predefined second subset of sense electrodes for the selected EEG test type or based on a set of rules for selecting the second subset of sense electrodes based on the first subset of sense electrodes. The signal processor 150 can then label all other sense electrodes as inactive.

By labeling each sense electrode and allocating each sense electrode to a particular "bucket," the signal processor 150 can prepare to: record sense signals from areas or channels of interest exclusively; maintain sense signals of interest with the dynamic range of sense electrodes in the first subset by tracking the DC component of the drive signal to the average center voltage of these sense signals of interest; and to calculate a virtual reference signal from other targeted sense electrodes in contact with the user's skin during the subsequent EEG test. The signal processor can also selectively deactivate sense electrodes and the controller 160 can selectively issue electrode adjustment prompts based on labels assigned to each sense electrode, as described below.

14.2 Dynamic Active Electrode Selection

In this variation, the signal processor 150 can also dynamically adjust the first and second subsets of sense electrodes throughout an EEG test. For example, the native EEG test application can enable the EEG test administrator to select and order multiple EEG test types into one composite EEG test and to then upload this composite EEG test to the EEG headset 102 for execution during a single session (i.e., one contiguous duration of time in which the EEG headset 102 is worn by one user). The EEG headset 102 can then implement methods and techniques described above to dynamically adjust the first and second subsets of sense electrodes as one EEG test is completed and a next EEG test is begun within the test session.

In the foregoing example, the EEG headset can: receive selection of a first EEG test specifying a first set of channels of interest and a first duration; and receive selection of a second EEG test specifying a second set of channels of interest and a second duration, wherein the second set of channels of interest differs from the first set of channels of interest. During execution of the first EEG test, the EEG headset 102 can: populate a first subset of sense electrodes corresponding to the first set of channels of interest; populate a second subset of sense electrodes matched to the first subset of sense electrodes; sample the first and second subsets of sense electrodes, as described above; and write the first set of sense signals to a first digital electroencephalography test result file corresponding to the first electroencephalography test over the first duration within a test period. The EEG headset 102 can also: select a third subset of sense electrodes corresponding to the second set of channels of interest; select a fourth subset of sense electrodes matched to the third set of sense electrodes; transition to reading sense signals from the third and fourth subsets of sense electrodes upon conclusion of the first duration within the test period; and write a third set of sense signals to a digital electroencephalography test result file corresponding to the second electroencephalography test over the second duration within the test period.

However, the EEG headset 102 can implement any other method or technique to automatically transition between preselected EEG tests within one EEG test session.

14.3 Dynamic Drive Signal

In this variation, the EEG headset 102 can map the DC component of the drive signal to a subset of sense electrodes, such as to the first subset of sense electrodes corresponding to channels of interest or an area of interest specified in the current EEG test. For example, in response to determining that a sense electrode in the first subset of sense electrodes has lost contact with the user's skin in Block S132 as described above, the signal processor 150 can remove the corresponding sense signal from the combination of sense signals calculated in Block S162 as described above. In this example, the EEG headset 102 can: read a first set of sense signals from the first subset of sense electrodes; determine improper contact between the user's skin and a first sense electrode in the first subset of sense electrodes in response to a first sense signal in the first set of sense signals excluding a first signal component oscillating at the reference frequency in Block S130; adjust the direct-current component of the drive signal to follow a combination of the first subset of sense signals—excluding the first sense signal—in response to detecting improper contact between the user's skin and the first sense electrode in Block S162; and transmit a prompt to adjust the first sense electrode to the EEG test administrator in Block S140. The signal processor 150 can therefore reject the corresponding sense signal from calculation of the DC component of the drive signal for the next sampling period such that the DC component of the drive signal follows the average of sense signals read from sense electrodes confirmed to be in proper contact with the user's skin.

Alternatively, in this implementation, the signal processor 150 can compile sense signals read from sense electrodes in both the first and second subsets of electrodes into a target DC value for the DC component of the drive signal such that sense signals read from these sense electrode—and written to a digital file and manipulated to calculate the virtual reference signal, respectively—remain approximately centered within the dynamic range of the EEG headset 102.

14.4 Notifications and Actions

In this variation, the EEG headset 102 can selectively respond to contact loss events at sense electrodes based on labels written to these sense electrodes before or during the EEG test.

In one implementation, when the signal processor 150 determines that a first sense electrode in the first subset of sense electrodes (i.e., corresponding to channels of interest for the current EEG test) has lost contact with the user's skin in Block S132, the EEG headset 102 can automatically remove a first sense signal—read from the first sense electrode—from calculation of a new target DC component of the drive signal in Blocks S161, S162, and S163. For example, in this variation, the EEG headset 102 can: receive selection of a set of channels of interest; select a first subset of sense electrodes—in a set of sense electrodes integrated into an electroencephalography headset—corresponding to the set of channels of interest; and output a drive signal through the driven electrode during a test period. In this example, the EEG headset 102 can then: read a first set of sense signals from the first subset of sense electrodes; calculate a first combination of the first set of sense signals; and adjust the direct-current component of the drive signal to follow the first combination over a first duration within the test period. Over a second duration within the test period, the EEG headset 102 can also: read a second set of sense signals from the first subset of sense electrodes; in response to a second sense signal read from a first sense electrode in the first subset of sense electrodes excluding a first signal component oscillating at the reference frequency, determine that the first sense electrode is in improper contact with the user's skin; calculate a second combination of the second set of sense signals, now excluding the second sense signal read from the first sense electrode; and adjust the direct-current component of the drive signal to follow the second combination.

In the foregoing implementation, the EEG headset 102 can also immediately broadcast a prompt to correct the first sense electrode in Block S140 when such loss of contact is detected. Because the first sense electrode corresponds to a channel of interest, the EEG headset 102 can continue to record the first sense signal to the digital file in Block S150 but annotate this channel, as described above. Alternatively, in order to reduce crosstalk between the first set and other active sense electrodes in the first subset or noise injection into these other channels due to the loss of skin contact at the first sense electrode, the EEG headset 102 can automatically deactivate the first sense electrode upon detection of loss of contact between the first sense electrode and the user's skin.

Similarly, when the signal processor 150 determines that a second sense electrode in the second subset of sense electrodes (i.e., active during the EEG test exclusively for calculation of a virtual reference signal) has lost contact with the user's skin in Block S132, the EEG headset 102 can automatically remove a second sense signal—read from the second sense electrode—from calculation of the virtual reference signal in Block S121. In this implementation, if more than a threshold number of sense electrodes in the second subset remain in proper contact with the user's skin when the second sense signal loses contact, the EEG headset 102 can: automatically deactivate the second sense electrode; and/or withhold transmission of a prompt to correct the second sense electrode to the EEG test administrator in Block S140. If the EEG headset 102 later determines that a first electrode in the first subset of sense electrode electrodes of interest has lost contact with the user's skin, the EEG headset 102 can append a prompt to correct the second sense electrode with a prompt to correct the first sense electrode and transmit the composite prompts to the EEG test administrator for rectification of both the first and second sense electrodes.

However, if fewer than the threshold number of sense electrodes in the second subset remain in proper contact with the user's skin when the second sense signal loses contact, the EEG headset 102 can immediately transmit such a prompt to correct the second sense electrode to the EEG test administrator in Block S140.

15. Remote Signal Processing

In one variation, the EEG headset 102 transmits electrode data (e.g., the digital reference signal and composite digital sense signals) to the remote external device substantially in real-time, and the external device implements methods and techniques described above to transform these electrode data into electrode contact qualities and to issue notifications—through its integrated display—to correct instances of poor electrode contact.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

We claim:

1. A method comprising:
   outputting a drive signal through a driven electrode in a set of electrical-biosignal electrodes coupled to an electroencephalography headset worn by a user, the drive signal comprising:
     an alternating-current component oscillating at a reference frequency; and
     a direct-current component at an initial direct-current value;
   reading a set of sense signals from a set of sense electrodes, in the set of electrical-biosignal electrodes, at a first time;
   calculating a first combination of the set of sense signals;
   calculating a first direct-current value comprising a combination of the first combination and the initial direct-current value of the direct-current component of the drive signal, the first direct-current value different from the initial direct-current value; and at a second time succeeding the first time, by a controller coupled to the electroencephalography headset, shifting the direct-current component of the drive signal output by the driven electrode from the initial direct current value to the first direct-current value to track a center voltage of the drive signal proximal a center of a dynamic range of the electroencephalography headset.

2. The method of claim 1:

further comprising, for each sense electrode in the set of sense electrodes, confirming proper contact between the user's skin and the sense electrode at the first time in response to a sense signal read from the sense electrode at the first time comprising a first signal component oscillating at the reference frequency; and wherein calculating the first combination of the set of sense signals comprises calculating the first combination of the set of sense signals, read from the set of sense electrodes, in response to confirming proper contact between the user's skin and each sense electrode in the set of sense electrodes.

3. The method of claim 1:

further comprising confirming proper contact between the user's skin and the driven electrode at the first time in response to the first combination comprising a second signal component oscillating at the reference frequency; and wherein shifting the direct-current component of the drive signal to the first direct-current value comprises shifting the direct-current component of the drive signal to the first direct-current value in response to confirming proper contact between the user's skin and the driven electrode.

4. The method of claim 2, further comprising:

for each sense electrode in a first subset of sense electrodes in the set of sense electrodes:
reading a second sense signal from the sense electrode at the second time; and
determining proper contact between the user's skin and the sense electrode at the second time in response to the second sense signal comprising the first signal component oscillating at the reference frequency;

for each sense electrode in a second subset of sense electrodes, distinct from the first subset of sense electrodes, in the set of sense electrodes:
reading a third sense signal from the sense electrode at the second time; and
determining improper contact between the user's skin and the sense electrode at the second time in response to the third sense signal excluding the first signal component oscillating at the reference frequency;

calculating a second combination of the first subset of sense signals;

calculating a second direct-current value comprising a combination of the second combination and the first direct-current value of the direct-current component of the drive signal; and at a third time succeeding the second time, shifting the direct-current component of the drive signal output by the driven electrode to the second direct-current value.

5. The method of claim 4, further comprising:

in response to determining improper contact between the user's skin and sense electrodes in the second subset of sense electrodes, generating an electronic notification comprising a prompt to adjust sense electrodes in the second subset of sense electrodes; and transmitting the electronic notification to an external computing device accessible by a biosignal test administrator.

6. The method of claim 5, further comprising, in response to confirmation by the biosignal test administrator of adjustment of sense electrodes in the second subset of sense electrodes:

reading a third set of sense signals from the set of sense electrodes at a fourth time succeeding the third time;
calculating a third combination of the set of sense signals;
calculating a third direct-current value comprising a combination of the third combination and the second direct-current value of the direct-current component of the drive signal; and
at a fifth time succeeding the fourth time, shifting the direct-current component of the drive signal output by the driven electrode to the third direct-current value.

7. The method of claim 1:

further comprising accessing a reference signal at the first time;
wherein calculating the first combination of the set of sense signals comprises:
for each sense signal in the set of sense signals, calculating a composite sense signal, in a set of composite sense signals, comprising the reference signal subtracted from the sense signal at the first time; and
calculating the first combination based on the first direct-current value of the direct-current component of the drive signal the set of composite sense signals.

8. The method of claim 7, wherein accessing the reference signal at the first time comprises:

reading a second set of sense signals from a cluster of sense electrodes, in the set of electrical-biosignal electrodes, at the first time, the cluster of sense electrodes offset and discrete from the set of electrodes; and
calculating the reference signal based on a combination of the second set of sense signals.

9. The method of claim , further comprising:

receiving an electroencephalography test type specifying a set of channels of interest;
selecting the set of sense electrodes corresponding to the set of channels of interest;
selecting the cluster of sense electrodes excluding sense electrodes in the set of sense electrodes, the cluster of sense electrodes forming a virtual reference electrode; and
storing the set of composite sense signals in a digital electroencephalography test result file.

10. The method of claim 9, wherein selecting the cluster of sense electrodes comprises populating the cluster of sense electrodes with sense electrodes integrated into an electroencephalography headset at locations correlated with limited muscle activity.

11. The method of claim 7:

wherein accessing the reference signal at the first time comprises reading the reference signal from a dedicated reference electrode; and
further comprising:
in response to the reference signal excluding a first signal component oscillating at the reference frequency and comprising a second signal component oscillating at an ambient frequency, detecting improper contact between the reference electrode and the user's skin;
in response to detecting improper contact between the reference electrode and the user's skin, generating an electronic notification comprising a prompt to adjust the reference electrode against the user's skin; and
transmitting the electronic notification to a computing device accessible by a biosignal test administrator.

12. The method of claim 7, further comprising:
in response to the reference signal comprising the first signal component oscillating at the reference frequency and excluding a second signal component oscillating at the ambient frequency, determining that the driven electrode is in proper contact with the user's skin; and
in response to determining that the driven electrode is in proper contact with the user's skin:
   indicating proper contact of the driven electrode in a virtual map of locations of the set of electrical-biosignal electrodes coupled to the electroencephalography headset; and
   serving the virtual map to a biosignal test administrator.

13. The method of claim 1:
wherein reading the set of sense signals from the set of sense electrodes comprises, for each sense electrode in the set of sense electrodes:
   reading a sense signal, in the set of sense signals, from the sense electrode at the first time; and
   detecting proper contact between the user's skin and the sense electrode at the first time in response to the first sense signal comprising a first signal component oscillating at the reference frequency;
wherein calculating the first combination of the set of sense signals comprises calculating the first combination of the set of sense signals in response to detecting proper contact between the user's skin and each sense electrode in the set of sense electrodes; and
further comprising:
   for each sense electrode in a second set of sense electrodes, distinct from the set of sense electrodes, in the set of electrical-biosignal electrodes:
      reading a second sense signal, in a second set of sense signals, from the sense electrode at the first time; and
      detecting improper contact between the user's skin and the sense electrode at the first time in response to the second sense signal excluding a second signal component oscillating at the reference frequency; and
   in response to detecting improper contact between the user's skin and the second set of sense electrodes:
      excluding the second set of sense signals from the first combination;
      generating an electronic notification comprising a prompt to adjust the second subset of sense electrodes against the user's head; and
      transmitting the electronic notification to a computing device accessible by a biosignal test administrator.

14. The method of claim 13:
wherein reading the set of sense signals from the set of sense electrodes comprises, for each sense electrode in the set of sense electrodes:
   reading a sense signal, in the set of sense signals, from the sense electrode at the first time; and
   detecting proper contact between the user's skin and the sense electrode at the first time in response to the first sense signal comprising a first signal component oscillating at the reference frequency;
wherein calculating the first combination of the set of sense signals comprises calculating the first combination of the set of sense signals in response to detecting proper contact between the user's skin and each sense electrode in the set of sense electrodes; and
further comprising:
   for each sense electrode in a second set of sense electrodes, distinct from the set of sense electrodes, in the set of electrical-biosignal electrodes:
      reading a second sense signal, in a second set of sense signals, from the sense electrode at the first time; and
      detecting improper contact between the user's skin and the sense electrode at the first time in response to the second sense signal excluding a second signal component oscillating at the reference frequency; and
   in response to detecting improper contact between the user's skin and the second set of sense electrodes:
      excluding the second set of sense signals from the first combination;
      indicating improper contact of the second subset of sense electrodes in a virtual map of locations of the set of electrical-biosignal electrodes coupled to the electroencephalography headset; and
      serving the virtual map to a biosignal test administrator.

15. A method for responding to changes in skin-contact quality of a set of electrical-biosignal electrodes against a head of a user, the method comprising:
outputting a drive signal through a driven electrode in the set of electrical-biosignal electrodes, the drive signal comprising an alternating-current component oscillating at a reference frequency and a direct-current component of a first direct-current value;
for each sense electrode in a first subset of sense electrodes in the set of electrical-biosignal electrodes:
   reading a first sense signal, in a first subset of sense signals, from the sense electrode at a first time; and
   detecting proper contact between the user's skin and the sense electrode at the first time in response to the first sense signal comprising a first signal component oscillating at the reference frequency;
for each sense electrode in a second subset of sense electrodes, distinct from the first subset of sense electrodes, in the set of electrical-biosignal electrodes:
   reading a second sense signal, in a second subset of sense signals, from the sense electrode at the first time; and
   detecting improper contact between the user's skin and the sense electrode at the first time in response to the second sense signal excluding a second signal component oscillating at the reference frequency;
calculating a first combination of the first subset of sense signals;
calculating a second direct-current value based on the first combination and the first direct-current value of the direct-current component of the drive signal;
at a second time succeeding the first time, shifting the direct-current component of the drive signal output by the driven electrode from the first direct current value to the second direct-current value;
in response to detecting improper contact between the user's skin and the second subset of sense electrodes, generating an electronic notification comprising a prompt to adjust the second subset of sense electrodes; and
transmitting the electronic notification to a computing device accessible by a biosignal test administrator.

16. The method of claim 15, wherein calculating the first combination of the first subset of sense signals comprises:
- calculating the first combination of the first subset of sense signals in response to detecting proper contact between the user's skin and the first subset of sense electrodes; and
- excluding the second subset of sense signals from the first combination in response to detecting improper contact between the user's skin and the second subset of sense electrodes.

17. A method for responding to changes in skin-contact quality of a set of electrical-biosignal electrodes against a head of a user, the method comprising:
- outputting a drive signal through a driven electrode in the set of electrical-biosignal electrodes, the drive signal comprising an alternating-current component oscillating at a reference frequency;
- for each sense electrode in a first subset of sense electrodes in the set of electrical-biosignal electrodes:
  - reading a first sense signal, in a first subset of sense signals, from the sense electrode at a first time; and
  - detecting proper contact between the user's skin and the sense electrode at the first time in response to the first sense signal comprising a first signal component oscillating at the reference frequency;
- for each sense electrode in a second subset of sense electrodes, distinct from the first subset of sense electrodes, in the set of electrical-biosignal electrodes:
  - reading a second sense signal, in a second subset of sense signals, from the sense electrode at the first time; and
  - detecting improper contact between the user's skin and the sense electrode at the first time in response to the second sense signal excluding a second signal component oscillating at the reference frequency;
- in response to detecting improper contact between the user's skin and the second subset of sense electrodes, generating an electronic notification comprising a prompt to adjust the second subset of sense electrodes; and
- transmitting the electronic notification to a computing device accessible by a biosignal test administrator.

18. The method of claim 17:
- wherein generating an electronic notification comprises, in response to detecting improper contact between the user's skin and the second subset of sense electrodes, indicating improper contact of the second subset of sense electrodes in a virtual map of locations of the set of electrical-biosignal electrodes coupled to the electroencephalography headset; and
- wherein transmitting the electronic notification to the computing device comprises serving the virtual map to the computing device.

19. The method of claim 17:
- wherein outputting the drive signal through the driven electrode comprises outputting the drive signal, through the driven electrode, comprising a direct-current component of a first direct-current value at the first time; and
- further comprising
  - calculating a first combination of the first subset of sense signals;
  - calculating a second direct-current value based on the first combination and the first direct-current value of the direct-current component of the drive signal; and
  - at a second time succeeding the first time, shifting the direct-current component of the drive signal output by the driven electrode from the first direct current value to the second direct-current value.

* * * * *